United States Patent
Johnson et al.

(10) Patent No.: US 9,498,164 B2
(45) Date of Patent: Nov. 22, 2016

(54) RECEIVERS FOR ANALYZING AND DISPLAYING SENSOR DATA

(71) Applicant: DexCom, Inc., San Diego, CA (US)

(72) Inventors: Eric Johnson, San Marcos, CA (US); Michael Robert Mensinger, San Diego, CA (US); Peter C. Simpson, Encinitas, CA (US); Thomas Hall, San Diego, CA (US); Hari Hampapuram, San Diego, CA (US); Kostyantyn Snisarenko, San Diego, CA (US); Eli Reihman, San Diego, CA (US); Holly Chico, San Diego, CA (US); Kassandra Constantine, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 400 days.

(21) Appl. No.: 14/098,366

(22) Filed: Dec. 5, 2013

(65) Prior Publication Data
US 2014/0091940 A1    Apr. 3, 2014

Related U.S. Application Data

(63) Continuation of application No. 13/026,163, filed on Feb. 11, 2011, now Pat. No. 9,041,730.

(60) Provisional application No. 61/304,337, filed on Feb. 12, 2010.

(51) Int. Cl.
*G06T 11/20*    (2006.01)
*A61B 5/00*    (2006.01)
(Continued)

(52) U.S. Cl.
CPC ............. *A61B 5/742* (2013.01); *A61B 5/0013* (2013.01); *A61B 5/1495* (2013.01); *A61B 5/14532* (2013.01); *A61B 5/743* (2013.01); *A61B 5/746* (2013.01); *A61B 5/7445* (2013.01); *A61B 5/7475* (2013.01); *G01N 33/66* (2013.01); *G06F 3/041* (2013.01); *G06F 3/0488* (2013.01);
(Continued)

(58) Field of Classification Search
CPC .......................... G06F 17/30716; G06T 11/20
See application file for complete search history.

(56) References Cited

U.S. PATENT DOCUMENTS 4,786,394 A    11/1988    Enzer et al.
5,343,869 A    9/1994    Pross et al.
(Continued)

FOREIGN PATENT DOCUMENTS

EP    1413245 A2    4/2004
EP    1688085 A1    8/2006
(Continued)

OTHER PUBLICATIONS

US 7,530,950, 05/2009, Brister et al. (withdrawn)
Bani Amer, M. M. 2002, An accurate amperometric glucose sensor based glucometer with eliminated cross-sensitivity. J Med Eng Technology 26(5):208-213.
(Continued)

*Primary Examiner* — Phi Hoang
(74) *Attorney, Agent, or Firm* — Knobbe Martens Olson & Bear, LLP

(57) ABSTRACT

This disclosure provides systems, methods and apparatus for processing, transmitting and displaying data received from an analyte sensor, such as a glucose sensor. The system may include a display device with at least one input device. In response to movement of or along the input device, the display device may change a glucose data output parameter and update an output of the display device using the changed output parameter.

16 Claims, 18 Drawing Sheets

(51) Int. Cl.

| | |
|---|---|
| *H04N 21/431* | (2011.01) |
| *G06T 3/00* | (2006.01) |
| *A61B 5/145* | (2006.01) |
| *G06F 3/0488* | (2013.01) |
| *G06F 3/041* | (2006.01) |
| *A61B 5/1495* | (2006.01) |
| *G01N 33/66* | (2006.01) |
| *G06F 19/00* | (2011.01) |
| *G06F 3/0484* | (2013.01) |

(52) U.S. Cl.
CPC ....... *G06F3/04847* (2013.01); *G06F 3/04883* (2013.01); *G06F 19/3406* (2013.01); *G06F 19/3468* (2013.01); *G06T 3/00* (2013.01); *G06T 11/20* (2013.01); *H04N 21/431* (2013.01)

(56) References Cited

U.S. PATENT DOCUMENTS

| | | |
|---|---|---|
| 5,497,772 A | 3/1996 | Schulman et al. |
| 5,660,163 A | 8/1997 | Schulman et al. |
| 5,791,344 A | 8/1998 | Schulman et al. |
| 5,810,770 A | 9/1998 | Chin et al. |
| 5,822,715 A | 10/1998 | Worthington et al. |
| 5,836,989 A | 11/1998 | Shelton |
| 5,867,688 A | 2/1999 | Simmon |
| 6,168,568 B1 | 1/2001 | Gavriely |
| 6,175,752 B1 | 1/2001 | Say et al. |
| 6,201,993 B1 | 3/2001 | Kruse et al. |
| 6,402,703 B1 | 6/2002 | Kensey et al. |
| 6,427,088 B1 | 7/2002 | Bowman et al. |
| 6,558,320 B1 | 5/2003 | Causey, III et al. |
| 6,558,351 B1 | 5/2003 | Steil et al. |
| 6,560,471 B1 | 5/2003 | Heller et al. |
| 6,565,509 B1 | 5/2003 | Say et al. |
| 6,579,690 B1 | 6/2003 | Bonnecaze et al. |
| 6,585,644 B2 | 7/2003 | Lebel et al. |
| 6,605,072 B2 | 8/2003 | Struys et al. |
| 6,641,533 B2 | 11/2003 | Causey, III et al. |
| 6,648,821 B2 | 11/2003 | Lebel et al. |
| 6,694,191 B2 | 2/2004 | Starkweather et al. |
| 6,699,218 B2 | 3/2004 | Flaherty et al. |
| 6,740,075 B2 | 5/2004 | Lebel et al. |
| 6,749,587 B2 | 6/2004 | Flaherty |
| 6,809,653 B1 | 10/2004 | Mann et al. |
| 6,810,290 B2 | 10/2004 | Lebel et al. |
| 6,813,519 B2 | 11/2004 | Lebel et al. |
| 6,948,492 B2 | 9/2005 | Wermeling et al. |
| 6,960,192 B1 | 11/2005 | Flaherty et al. |
| 6,978,171 B2 | 12/2005 | Goetz et al. |
| 6,990,366 B2 | 1/2006 | Say et al. |
| 7,003,341 B2 | 2/2006 | Say et al. |
| 7,025,743 B2 | 4/2006 | Mann et al. |
| 7,092,891 B2 | 8/2006 | Maus et al. |
| 7,098,803 B2 | 8/2006 | Mann et al. |
| 7,190,988 B2 | 3/2007 | Say et al. |
| 7,267,665 B2 | 9/2007 | Steil et al. |
| 7,310,544 B2 | 12/2007 | Brister et al. |
| 7,343,565 B2 | 3/2008 | Ying et al. |
| 7,344,500 B2 | 3/2008 | Talbot et al. |
| 7,354,420 B2 | 4/2008 | Steil et al. |
| 7,366,556 B2 | 4/2008 | Brister et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,494,465 B2 | 2/2009 | Brister et al. |
| 7,497,827 B2 | 3/2009 | Brister et al. |
| 7,615,007 B2 | 11/2009 | Shults et al. |
| 7,640,048 B2 | 12/2009 | Dobbles et al. |
| 7,651,596 B2 | 1/2010 | Petisce et al. |
| 7,653,582 B2 * | 1/2010 | Costache ............ G06Q 40/00 705/35 |
| 7,654,956 B2 | 2/2010 | Brister et al. |
| 7,831,287 B2 | 11/2010 | Brister et al. |
| 7,857,760 B2 | 12/2010 | Brister et al. |
| 7,873,595 B2 | 1/2011 | Singh et al. |
| 7,899,511 B2 | 3/2011 | Shults et al. |
| 7,901,354 B2 | 3/2011 | Shults et al. |
| 7,949,381 B2 | 5/2011 | Brister et al. |
| 8,133,178 B2 | 3/2012 | Brauker et al. |
| 8,170,803 B2 | 5/2012 | Kamath et al. |
| 8,233,959 B2 | 7/2012 | Kamath et al. |
| 8,736,611 B1 * | 5/2014 | Tulasi ............... G06T 11/206 345/440 |
| 2002/0178126 A1 | 11/2002 | Beck et al. |
| 2002/0198513 A1 | 12/2002 | Lebel et al. |
| 2003/0100040 A1 | 5/2003 | Bonnecaze et al. |
| 2003/0100821 A1 | 5/2003 | Heller et al. |
| 2003/0114836 A1 | 6/2003 | Estes et al. |
| 2003/0130616 A1 | 7/2003 | Steil et al. |
| 2003/0187338 A1 | 10/2003 | Say et al. |
| 2003/0203498 A1 | 10/2003 | Neel et al. |
| 2004/0010207 A1 | 1/2004 | Flaherty et al. |
| 2004/0027349 A1 * | 2/2004 | Landau ............ G06F 17/30572 345/440 |
| 2004/0068230 A1 | 4/2004 | Estes et al. |
| 2004/0106859 A1 | 6/2004 | Say et al. |
| 2004/0128225 A1 | 7/2004 | Thompson et al. |
| 2004/0167801 A1 | 8/2004 | Say et al. |
| 2004/0186365 A1 | 9/2004 | Jin et al. |
| 2004/0193025 A1 | 9/2004 | Steil et al. |
| 2004/0236200 A1 | 11/2004 | Say et al. |
| 2005/0044088 A1 | 2/2005 | Lindsay et al. |
| 2005/0065464 A1 | 3/2005 | Talbot et al. |
| 2005/0121322 A1 | 6/2005 | Say et al. |
| 2005/0143635 A1 | 6/2005 | Kamath et al. |
| 2005/0195930 A1 | 9/2005 | Spital et al. |
| 2005/0203360 A1 | 9/2005 | Brauker et al. |
| 2006/0001550 A1 | 1/2006 | Mann et al. |
| 2006/0010098 A1 | 1/2006 | Goodnow et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0142651 A1 | 6/2006 | Brister et al. |
| 2006/0155180 A1 | 7/2006 | Brister et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189863 A1 | 8/2006 | Peyser et al. |
| 2006/0195029 A1 | 8/2006 | Shults et al. |
| 2006/0200020 A1 | 9/2006 | Brister et al. |
| 2006/0200970 A1 | 9/2006 | Brister et al. |
| 2006/0222566 A1 | 10/2006 | Brauker et al. |
| 2006/0229512 A1 | 10/2006 | Petisce et al. |
| 2006/0235285 A1 | 10/2006 | Brister et al. |
| 2006/0258929 A1 | 11/2006 | Goode et al. |
| 2007/0016381 A1 | 1/2007 | Kamath et al. |
| 2007/0027383 A1 | 2/2007 | Peyser et al. |
| 2007/0027384 A1 | 2/2007 | Brister et al. |
| 2007/0027385 A1 | 2/2007 | Brister et al. |
| 2007/0032717 A1 | 2/2007 | Brister et al. |
| 2007/0038044 A1 | 2/2007 | Dobbles et al. |
| 2007/0059196 A1 | 3/2007 | Brister et al. |
| 2007/0066873 A1 | 3/2007 | Kamath et al. |
| 2007/0093704 A1 | 4/2007 | Brister et al. |
| 2007/0129621 A1 | 6/2007 | Kellogg et al. |
| 2007/0163880 A1 | 7/2007 | Woo et al. |
| 2007/0173709 A1 | 7/2007 | Petisce et al. |
| 2007/0173710 A1 | 7/2007 | Petisce et al. |
| 2007/0176867 A1 | 8/2007 | Reggiardo et al. |

(56) References Cited

U.S. PATENT DOCUMENTS

| | | |
|---|---|---|
| 2007/0197889 A1 | 8/2007 | Brister et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213610 A1 | 9/2007 | Say et al. |
| 2007/0213611 A1 | 9/2007 | Simpson et al. |
| 2007/0232879 A1 | 10/2007 | Brister et al. |
| 2007/0235331 A1 | 10/2007 | Simpson et al. |
| 2007/0255114 A1 | 11/2007 | Ackermann et al. |
| 2008/0072663 A1 | 3/2008 | Keenan et al. |
| 2008/0086040 A1 | 4/2008 | Heller et al. |
| 2008/0086041 A1 | 4/2008 | Heller et al. |
| 2008/0086042 A1 | 4/2008 | Brister et al. |
| 2008/0086043 A1 | 4/2008 | Heller et al. |
| 2008/0086044 A1 | 4/2008 | Brister et al. |
| 2008/0086273 A1 | 4/2008 | Shults et al. |
| 2008/0091094 A1 | 4/2008 | Heller et al. |
| 2008/0091095 A1 | 4/2008 | Heller et al. |
| 2008/0108942 A1 | 5/2008 | Brister et al. |
| 2008/0119703 A1 | 5/2008 | Brister et al. |
| 2008/0119704 A1 | 5/2008 | Brister et al. |
| 2008/0119706 A1 | 5/2008 | Brister et al. |
| 2008/0188731 A1 | 8/2008 | Brister et al. |
| 2008/0194935 A1 | 8/2008 | Brister et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0218180 A1 | 9/2008 | Waffenschmidt et al. |
| 2008/0234322 A1 | 9/2008 | Syroid |
| 2008/0242961 A1 | 10/2008 | Brister et al. |
| 2008/0255438 A1 | 10/2008 | Saidara et al. |
| 2008/0262469 A1 | 10/2008 | Brister et al. |
| 2008/0275313 A1 | 11/2008 | Brister et al. |
| 2008/0296155 A1 | 12/2008 | Shults et al. |
| 2008/0306435 A1 | 12/2008 | Kamath et al. |
| 2008/0306444 A1 | 12/2008 | Brister et al. |
| 2009/0018123 A1 | 1/2009 | Sindkhedkar et al. |
| 2009/0018424 A1 | 1/2009 | Kamath et al. |
| 2009/0036758 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0063964 A1 | 3/2009 | Huang et al. |
| 2009/0076356 A1 | 3/2009 | Simpson |
| 2009/0076360 A1 | 3/2009 | Brister et al. |
| 2009/0076361 A1 | 3/2009 | Kamath et al. |
| 2009/0099436 A1 | 4/2009 | Brister et al. |
| 2009/0124879 A1 | 5/2009 | Brister et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0240120 A1 | 9/2009 | Mensinger et al. |
| 2010/0047745 A1 | 2/2010 | Bergqwist |
| 2010/0095229 A1* | 4/2010 | Dixon .......... A61B 5/1411 715/763 |
| 2010/0257490 A1 | 10/2010 | Lyon et al. |
| 2011/0105955 A1 | 5/2011 | Yudovsky et al. |
| 2011/0201911 A1 | 8/2011 | Johnson et al. |
| 2011/0219325 A1* | 9/2011 | Himes .......... G06F 19/3406 715/771 |
| 2011/0271172 A1* | 11/2011 | Radakovitz .......... G06F 17/246 715/212 |
| 2012/0017165 A1* | 1/2012 | Gardner .......... G06F 17/30899 715/771 |
| 2012/0203089 A1* | 8/2012 | Rule .......... A61B 5/0002 600/366 |

FOREIGN PATENT DOCUMENTS

| | | |
|---|---|---|
| EP | 1918837 A1 | 5/2008 |
| EP | 1972270 A1 | 9/2008 |
| EP | 1949849 B1 | 9/2009 |
| WO | WO 90/10861 | 9/1990 |
| WO | WO 98/24358 | 6/1998 |
| WO | WO 99/04043 | 1/1999 |
| WO | WO 99/56613 | 4/1999 |
| WO | WO 00/19887 | 4/2000 |
| WO | WO 00/32098 | 6/2000 |
| WO | WO 00/74753 | 12/2000 |
| WO | WO 00/78210 | 12/2000 |
| WO | WO 01/52727 | 7/2001 |
| WO | WO 01/52935 | 7/2001 |
| WO | WO 01/54753 | 8/2001 |
| WO | WO 02/058537 | 8/2002 |
| WO | WO 02/100262 | 12/2002 |
| WO | WO 03/008013 | 1/2003 |
| WO | WO 03/008014 | 1/2003 |
| WO | WO 03/009207 | 1/2003 |
| WO | WO 03/009208 | 1/2003 |
| WO | WO 03/022327 | 3/2003 |
| WO | WO 03/053498 | 7/2003 |
| WO | WO 2004/008956 | 1/2004 |
| WO | WO 2004/009161 | 1/2004 |
| WO | WO 2004/042382 | 5/2004 |
| WO | WO 2004/060455 | 7/2004 |
| WO | WO 2004/061420 | 7/2004 |
| WO | WO 2005/057168 | 6/2005 |
| WO | WO 2005/057175 | 6/2005 |
| WO | WO 2005/067797 | 7/2005 |
| WO | WO 2005/089103 | 9/2005 |
| WO | WO 2006/001929 | 1/2006 |
| WO | WO 2006/019623 | 2/2006 |
| WO | WO 2006/020212 | 2/2006 |
| WO | WO 2006/021430 | 3/2006 |
| WO | WO 2006/066926 | 6/2006 |
| WO | WO 2006/081975 | 8/2006 |
| WO | WO 2006/083831 | 8/2006 |
| WO | WO 2006/105146 | 10/2006 |
| WO | WO 2007/005170 | 1/2007 |
| WO | WO 2007/005219 | 1/2007 |
| WO | WO 2007/033010 | 3/2007 |
| WO | WO 2007/038464 | 4/2007 |
| WO | WO 2007/053497 | 5/2007 |
| WO | WO 2007/053832 | 5/2007 |
| WO | WO 2007/059061 | 5/2007 |
| WO | WO 2007/065285 | 6/2007 |
| WO | WO 2007/086997 | 8/2007 |
| WO | WO 2007/097754 | 8/2007 |
| WO | WO 2007/101260 | 9/2007 |
| WO | WO 2007/126920 | 11/2007 |
| WO | WO 2007/130239 | 11/2007 |
| WO | WO 2008/003003 | 11/2007 |
| WO | WO 2008/016501 | 2/2008 |
| WO | WO 2008/021913 | 2/2008 |
| WO | WO 2008/028644 | 3/2008 |
| WO | WO 2008/042760 | 4/2008 |
| WO | WO 2008/048452 | 4/2008 |
| WO | WO 2008/052057 | 5/2008 |
| WO | WO 2008/052199 | 5/2008 |
| WO | WO 2008/052374 | 5/2008 |
| WO | WO 2008/054608 | 5/2008 |
| WO | WO 2008/055037 | 5/2008 |
| WO | WO 2008/067314 | 6/2008 |
| WO | WO 2008/069931 | 6/2008 |
| WO | WO 2008/079616 | 7/2008 |
| WO | WO 2008/092286 | 8/2008 |
| WO | WO 2008/094249 | 8/2008 |
| WO | WO 2008/101211 | 8/2008 |
| WO | WO 2008/101217 | 8/2008 |

(56) References Cited

FOREIGN PATENT DOCUMENTS

| WO | WO 2008/101229 | 8/2008 |
|---|---|---|
| WO | WO 2008/116329 | 10/2008 |
| WO | WO 2008/128210 | 10/2008 |
| WO | WO 2008/130895 | 10/2008 |
| WO | WO 2008/130896 | 10/2008 |
| WO | WO 2008/130897 | 10/2008 |
| WO | WO 2008/130898 | 10/2008 |
| WO | WO 2008/134561 | 11/2008 |
| WO | WO 2008/134587 | 11/2008 |
| WO | WO 2008/138006 | 11/2008 |
| WO | WO 2008/150633 | 12/2011 |

OTHER PUBLICATIONS

Biermann et al. 2008. How would patients behave if they were continually informed of their blood glucose levels? A simulation study using a "virtual" patient. Diabetes Technology & Therapeutics 10:178-187.

McGrath et al. 1995. The use of differential measurements with a glucose biosensor for interference compensation during glucose determinations by flow injection analysis. Biosensros & Bioelectronics 10:937-943.

Thome-Duret et al. 1998. Continous Glucose Monitoring in the Free-Moving Rat. Metabolism 47(7):799-803.

Wood, et al. Mar. 1990. Hermetic Sealing with Epoxy. Mechanical Engineering 1-3.

* cited by examiner

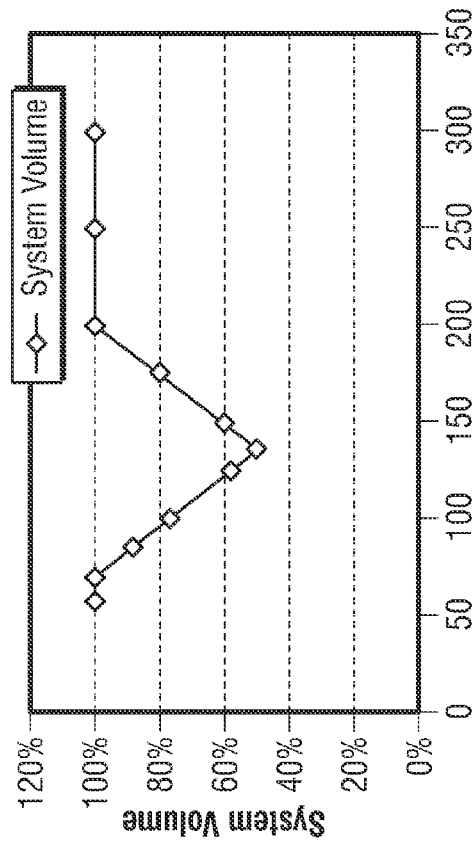

| mg/dL | Notes | System Volume | Notes |
|---|---|---|---|
| 300 | | 100% | Anything Above High Limit is 100% |
| 250 | | 100% | Anything Above High Limit is 100% |
| 200 | User Set High Glucose Limit | 100% | |
| 175 | | 80.8% | Linear Interpolation from Average Glucose to High Glucose |
| 150 | | 61.5% | Linear Interpolation from Average Glucose to High Glucose |
| 135 | Average of High & Low Glucose Limit | 50% | |
| 125 | | 57.7% | Linear Interpolation from Average Glucose to Low Glucose |
| 100 | | 76.9% | Linear Interpolation from Average Glucose to Low Glucose |
| 85 | | 88.5% | Linear Interpolation from Average Glucose to Low Glucose |
| 70 | User Set Low Glucose Limit (User Set) | 100% | |
| 60 | | 100% | Anything Below Low Limit is 100% |

RECEIVERS FOR ANALYZING AND DISPLAYING SENSOR DATA

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 13/026,163, filed Feb. 11, 2011, which claims the benefit of U.S. Provisional Application No. 61/304,337, filed Feb. 12, 2010. Each of the aforementioned applications is incorporated by reference herein in its entirety, and each is hereby expressly made a part of this specification.

FIELD

The present invention relates generally to systems and methods for processing, transmitting and displaying data received from an analyte sensor, such as a glucose sensor.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is going up (higher) or down (lower) based on conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display.

SUMMARY

Various implementations of systems, methods and devices within the scope of the appended claims each have several aspects, no single one of which is solely responsible for the desirable attributes described herein. Without limiting the scope of the appended claims, some prominent features are described herein.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

In one embodiment, a glucose monitoring system comprises a display device configured to receive displayable sensor information from a sensor electronics module physically connected to a continuous analyte sensor. The display device may comprise a storage device configured to store at least some of the displayable sensor information, a display; and at least one input device. The display device is configured to detect movement of or along the at least one input device, and is configured to change a glucose data output parameter in response to the detected movement. Furthermore, the display device is configured to update an output of glucose data using the changed glucose data output parameter.

In another embodiment, a computerized method for displaying glucose information on a display device in a glucose monitoring system comprises detecting movement of or along at least one input device, changing a glucose data output parameter in response to the detected movement, and updating an output of the display device using the glucose data output parameter.

In another embodiment, a computer readable medium has stored thereon instructions that when executed by a processor in a glucose monitoring system comprising a display device with at least one input device, cause the processor to detect movement of or along the at least one input device, change a glucose data output parameter in response to the detected movement, and update an output of the display device using the changed glucose data output parameter.

BRIEF DESCRIPTION OF THE DRAWINGS

FIGS. 15A and 15B show examples of alarm volume levels which correspond to certain glucose level readings.

Figure 1:
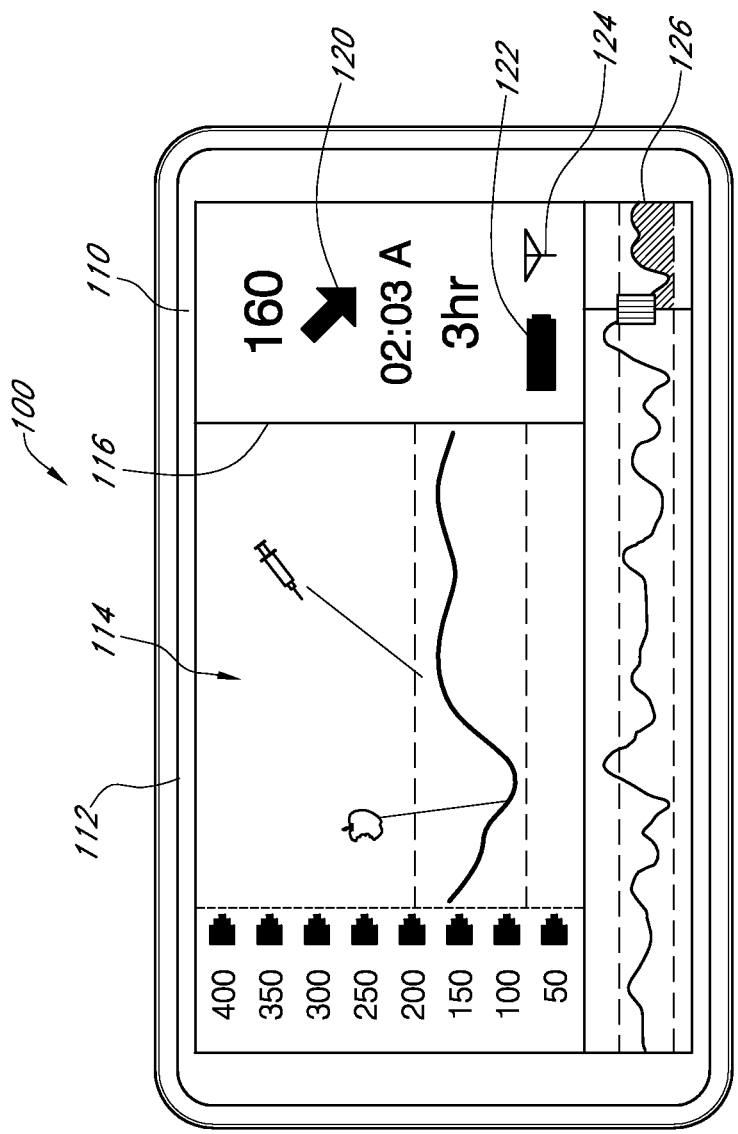
FIG. 1 shows an example of a top view of an exemplary touch sensitive receiver displaying various information associated with sensor data.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

Various aspects of implementations within the scope of the appended claims are described below. It should be apparent that the aspects described herein may be implemented in a wide variety of forms and that any specific structure and/or function described herein is merely illustrative. Based on the present disclosure a person/one having ordinary skill in the art should appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structure and/or functionality in addition to or other than one or more of the aspects set forth herein.

The word "exemplary" is used herein to mean "serving as an example, instance, or illustration." Any implementation described herein as "exemplary" is not necessarily to be construed as preferred or advantageous over other implementations. The following description is presented to enable any person skilled in the art to make and use the invention. Details are set forth in the following description for purpose of explanation. It should be appreciated that one of ordinary skill in the art would realize that the invention may be practiced without the use of these specific details. In other instances, well known structures and processes are not elaborated in order not to obscure the description of the invention with unnecessary details. Thus, the present invention is not intended to be limited by the implementations shown, but is to be accorded with the widest scope consistent with the principles and features disclosed herein.

DEFINITIONS

In order to facilitate an understanding of the systems and methods discussed herein, a number of terms are defined below. The terms defined below, as well as other terms used herein, should be construed to include the provided definitions, the ordinary and customary meaning of the terms, and any other implied meaning for the respective terms. Thus, the definitions below do not limit the meaning of these terms, but only provide exemplary definitions.

The terms "processor module," "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes instructions that drive a computer. A processor may include a conventional processor, such as a processor of a desktop, notebook, or mobile computing devices; an application specific integrated circuit (ASIC); a field programmable gate array (FPGA); or any other suitable processing hardware.

The term "sensor" as used herein is a broad term and is to be given its ordinary and customary meaning to a person of ordinary skill in the art (and is not to be limited to a special or customized meaning), and furthermore refers without limitation to any device (or portion of a device) that measures a physical quantity and converts it into a signal that can be processed by analog and/or digital circuitry, such as a processor. Thus, the output of a sensor may be an analog and/or digital signal. Examples of sensors include analyte sensors, glucose sensors, temperature sensors, altitude sensors, accelerometers, blood pressure, and heart rate (e.g., pulse) sensors.

The term "glucose sensor" as used herein is a broad term and is to be given its ordinary and customary meaning to a person of ordinary skill in the art (and are not to be limited to a special or customized meaning), and furthermore refer without limitation to any sensor by which glucose can be quantified (e.g., enzymatic or non-enzymatic). For example, some embodiments of a glucose sensor may utilize a membrane that contains glucose oxidase that catalyzes the conversion of oxygen and glucose to hydrogen peroxide and gluconate, as illustrated by the following chemical reaction:

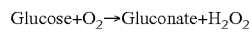

$$Glucose + O_2 \rightarrow Gluconate + H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The term "sensor data", as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor, a pulse sensor, a temperature sensor, or any other biological or other sensor. In the case of a continuous analyte sensor, sensor data may include a raw data stream, or simply data stream, of analog or digital signal directly related to a measured analyte from an analyte sensor (or other signal received from another sensor), as well as calibrated and/or filtered raw data. Sensor data may include calibrated data, smoothed data, filtered data, transformed data, and/or any other data associated with a sensor.

The term "algorithm" as used herein is a broad term and is to be given its ordinary and customary meaning to a person of ordinary skill in the art (and is not to be limited to a special or customized meaning), and furthermore refers without limitation to a computational process (associated with computer programming or other written instructions) involved in transforming information from one state to another.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to a mammal, such as a human, that is implanted with a device, such as a sensor.

The term "continuous analyte sensor" as used herein is a broad term and is to be given its ordinary and customary meaning to a person of ordinary skill in the art (and is not to be limited to a special or customized meaning), and furthermore refers without limitation to a device, or portion of a device, that continuously or continually measures a concentration of an analyte, for example, at time intervals ranging from fractions of a second up to, for example, 1, 2, or 5 minutes, or longer. In one exemplary embodiment, a glucose sensor comprises a continuous analyte sensor, such as is described in U.S. Pat. No. 7,310,544, which is incorporated herein by reference in its entirety.

The term "alarm" as used herein is a broad term, and is to be given its ordinary and customary meaning to a person of ordinary skill in the art (and is not to be limited to a special or customized meaning), and furthermore refers without limitation to an alert or signal, such as an audible, visual, and/or tactile signal, triggered in response to one or more alarm conditions. For example, in one embodiment, hyperglycemic and hypoglycemic alarms are triggered when present or predicted clinical danger is assessed based on continuous analyte data.

The term "receiver" as used herein is a broad term, and is to be given its ordinary and customary meaning to a person of ordinary skill in the art (and is not to be limited to a special or customized meaning), and furthermore refers without limitation to a device that receives sensor data from a sensor, either directly from the sensor (e.g., via a wired or wireless communication link) or indirectly from another device. A receiver typically includes one or more processor, a computer readable storage medium (such as one or more volatile and/or non-volatile storage device), one or more displays, and one or more input devices. Various input devices of a receiver are discussed below, some of which are integrated into displays of receivers. In addition to including circuitry for communicating with one or more sensors, a receiver may also include communication circuitry for communicating with other devices, such as telephony circuitry that allows transmission of short messaging service (SMS) messages or voice communications, and/or a network interface that allows TCP/IP communications across one or more networks, including the Internet. A receiver typically executes software that controls operations of the receiver.

Illustrative Receivers

FIG. 1 is a top view of an exemplary touch sensitive receiver 100 displaying various information associated with sensor data from a continuous blood glucose sensor. For example, the user interface 110 displayed on the receiver 100 includes a three hour glucose chart 114, a trend direction indicator 120, a remaining battery life indicator 122, a signal strength indicator 124, and a navigation bar 126. In this embodiment, the glucose chart 114 displays sensor data from a continuous analyte sensor in a graph format. In one embodiment, the three hour period ends with the last sensor data received from the continuous glucose sensor by default. In some embodiments, the three hour period is selectable by the user (e.g., to select any previous three hour period), such as using any of the input devices discussed below. In some embodiments, the glucose chart 114 may include one or more tick marks and/or other indicia on the x-axis that provide indications of quantity and/or units that are displayed. For example, the x-axis may include periodic tick marks (and/or labels) that mark each hour (or any other time period) of data illustrated.

In the embodiment of FIG. 1, the trend direction indicator 120 indicates a current trend in the direction of the glucose levels of the host. The trend direction indicator 120 may indicate (by default) a trend over a set time period, such as 15 minutes. In certain embodiments, the time period of sensor data considered in calculating the trend direction indicator 120 may be customized by the user of the receiver to include sensor data from any other time period. The signal strength indicator 124 indicates strength of a communication signal between the receiver 100 and one or more corresponding sensor(s). In an embodiment where the receiver is in communication with multiple sensors, multiple signal strength indicators may be included in a user interface displayed on the receiver, and/or signal strength indicators for respective sensors may be alternatively displayed on the receiver display. For example, the display of a receiver may automatically cycle between the various signal strength indicators at a predetermined interval, such as 2 or 5 seconds, or in response to a particular input from the input device, such as the user touching a currently displayed signal strength depicted in a touch sensitive display indicator to indicate that a signal strength indicator for another sensor should be displayed in place of the current indicator.

Figure 7:
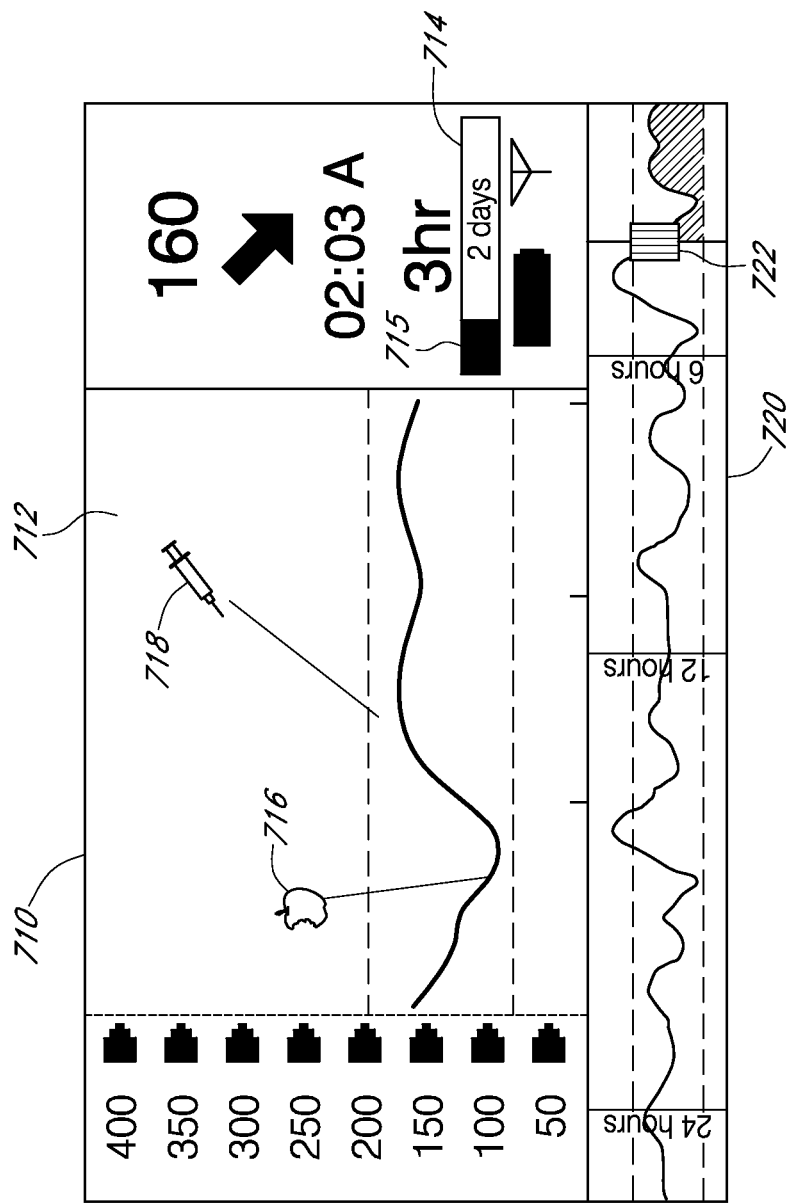
FIG. 7 shows an example of a user interface including a glucose chart for a three hour time period and a navigation bar that shows glucose data over a longer time period.

In the embodiment of FIG. 1, the navigation bar 126 displays glucose levels of the host over an extended time period and allows a user of the receiver 100 to easily change the time period for which sensor data is displayed in the glucose chart 114. FIG. 7 illustrates a similar navigation bar and the discussion of FIG. 7, below, includes further details regarding operation and use of a navigation bar.

Figure 1A:
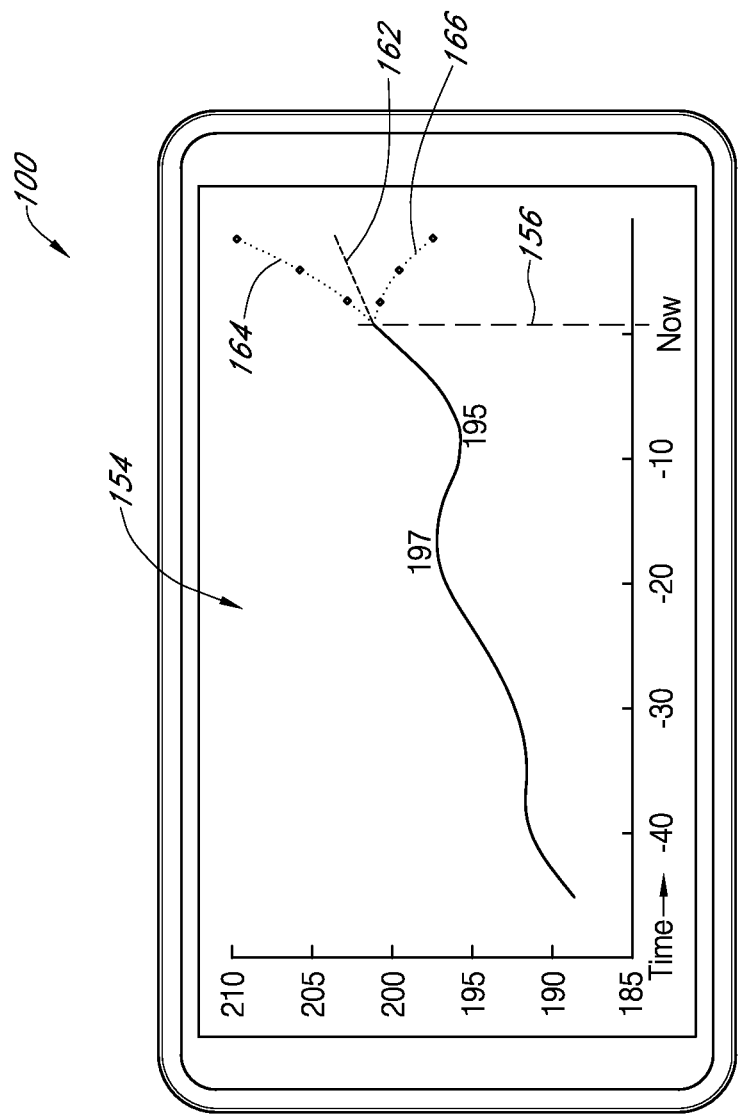
FIG. 1A shows an example of a glucose chart showing glucose levels of a host over a determined time period.

FIG. 1A illustrate the receiver 100 with a glucose chart 154 that covers substantially the entire display of the receiver 100 and includes an estimate of where the host's glucose level will go to in the future. In one embodiment, glucose charts can be selected to fill the entire (or substantially the entire) display of a receiver, including the receiver 100, 200, 410, 420, 430, and any other receiver, in response to any predefined user input, such as tapping a displayed glucose chart in a predefined manner (e.g., a single or double tap, a pinch or spread motion on a touch sensitive display, or selections of a hardware button or other input device). Thus, more glucose data and/or details of glucose data may be viewed by the user in response to activating a "full screen display" of a glucose chart. In one embodiment, when the display currently shows the glucose chart in full screen mode (e.g. FIG. 1A), display of other information may be selectively overlaid on the display in response to a predefined input by the user, such as moving a receiver with one or more motion sensors (e.g., accelerometers) in a predefined direction and/or pattern. Thus, the additional information in pane 116 of FIG. 1 (that is not included in the full screen display of FIG. 1A) may be overlaid on the glucose chart of FIG. 1A by the predefined user input, and removed from display by another predefined user input or after a predetermined time, for example.

In some embodiments, any other pane, such as the pane 116 of FIG. 1 that displays the trend direction indicator 120, the remaining battery life indicator 122, the signal strength indicator 124, and the navigation bar 126, may be selected for full screen display by similar predefined user inputs discussed above. Additionally, in some embodiment, the user may customize the types of information that are displayed in certain panes, as well as customize which panes are selected for concurrent display. In some embodiment, the user can also define an action for certain user inputs, such as whether a full screen display of the current glucose chart should appear in response to a particular user input or if a pane including current status information should be displayed on the display (e.g., in a pop-up window) in response to the particular user input. In one embodiment, various panes that may be displayed on the receiver (e.g., various glucose charts, status windows, setup information, training information) may be moved about the display screen in order to allow customization of positions of the various panes. Thus, the user may be provided with the ability to customize what is displayed on the receiver at various times and in response to various inputs.

In the example of FIG. 1A, the glucose charts shows glucose levels of a host over a time period of about 45 minutes. The current glucose level of the host is shown by line 156 and a predicted range of future levels is displayed to the right of the current level line 156. In one embodiment, the most likely estimated glucose values are indicated by line 162, which may be determined in a realtime manner using any portion of previous glucose data of the host, as well as any other relevant data regarding the host that the receiver has access to. In the embodiment of FIG. 1A, a predicted variation of estimated glucose values are indicated by an upper limit 164 and a lower limit 166, which together form a cone of possibilities for the host's glucose levels over a subsequent time period (e.g., 15, 30, or 60 minutes or more). Depending on the embodiment, the cone of possibilities may be determined with varying confidence levels, such as a 95% confidence level that the host's glucose level will be within the upper and lower limits 164, 166 in the estimated time period. In some embodiments, the user may be allowed to adjust the confidence level (either higher or lower than 95%), the estimated time period (e.g., between 5 minutes and 6 hours), and/or provide additional information that might be used in calculating the estimated glucose levels (e.g., the user may have indicated a regularly scheduled workout that occurs within a glucose estimation period such that the receiver compensates for the intended workout accordingly). U.S. patent application Ser. No. 11/007,920, titled "Signal processing for continuous analyte sensor," which is hereby incorporated by reference in its entirety, describes further details regarding calculation and display of estimated glucose values.

In the embodiment of FIG. 1, the receiver 100 comprises hardware that allows the user to control operations of the receiver 100 by touching the display of the receiver 100. Thus, the input device of the receiver 100 is part of, or is coupled directly to, the display of the receiver 100. For example, the receiver 100 may include a touch sensitive surface that is resistive or capacitive, or that uses surface acoustic waves to determine when an object (e.g., a user's finger, a stylus, or other object) touches or is very close to the display. Many touch sensitive displays may also determine a force applied by the touching (e.g., determine whether the user softly touched the display or pushed hard on the display), a direction, speed, and/or acceleration of movement of a user's finger across the display, and/or whether multiple locations on the display are touched. Each of these attributes of a user's interfacing with a touch sensitive display may be used to indicate variations on commands associated with a particular touching, or may indicate completely different commands. For example, a single finger touch on the glucose chart 114 may indicate to the receiver software that the user wants to set options for display of data, and may result in an options user interface being displayed in place of the glucose chart 114. However, if the receiver detects two fingers touching the glucose chart 114, the software may be programmed to zoom in on the displayed chart in response to the user's fingers moving further apart and to zoom out on the displayed chart in response to the user's fingers moving closer together. Additionally, a touch sensitive display (or any other input device discussed herein) may be used to scroll linearly through glucose data over time, zoom in and out of sections of glucose data, scroll point-to-point within a graph to see individual values, and the like. Thus, an endless combination of commands may be provided through a touch sensitive display in response to the above-noted attributes that may be detected by a touch sensitive display.

A resistive touch sensitive display may include layers that are separated by a small gap such that when a user's finger touches a particular portion of the surface the two layers are brought into contact in order to cause an electrical current to run through layers at that particular position. The position where the current is detected on the resistive surface may then be used to determine a particular screen position where the surface was touched. The screen position touched may then be used by the receiver's software to determine any processes to be performed in response to the detected touching of the display (e.g., displaying a signal strength indicator for a second sensor in response to determining that the user touched the signal strength indicator for a first sensor).

In a capacitive system, one layer of the display stores a capacitive charge that is transferred to a user's finger (or other object) that is in contact with (or in very close proximity to) the touch sensitive display. Thus, the position on the surface where a reduced charge is detected can be translated into coordinates of the display where the user is interacting with the touch sensitive surface.

A surface acoustic wave system may include at least two transducers, one for receiving and one for transmitting acoustic signals. In one embodiment, the transducers are placed along the X and Y axes of a touch sensitive display, with mirrors on the opposite sides of the touch sensitive display. The receiving transducer is configured to detect when a portion of the wave has been disturbed by an object, such as a user's finger or stylus, and to determine based on disturbance in the wave a specific position where the object touched or moved near to the touch sensitive surface.

Figure 2A:
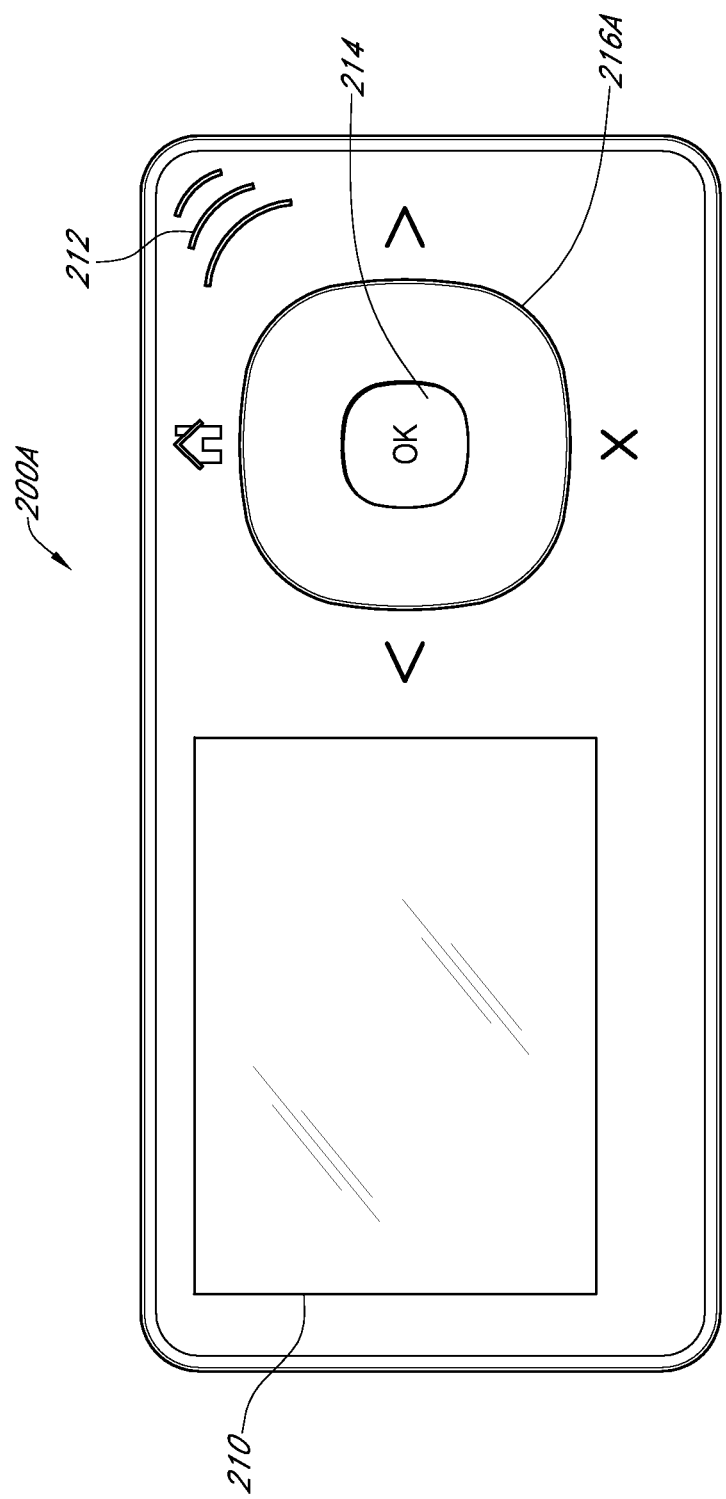
FIGS. 2A and 2B show examples of top views of two different exemplary receivers having substantially circular touch sensitive input devices.
Figure 2B:
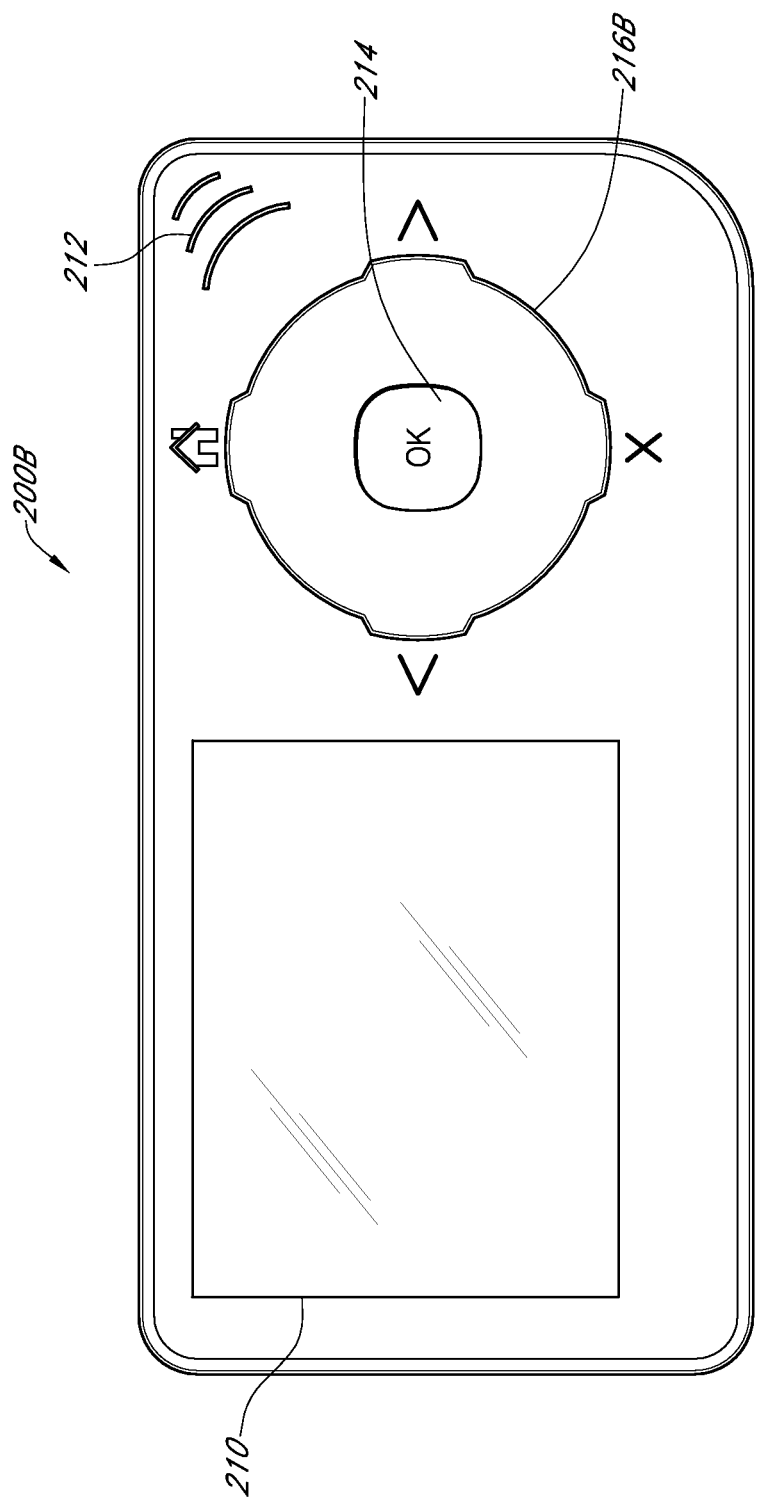

FIGS. 2A and 2B are top views of two different receivers 200A and 200B (collectively referred to as receivers 200) having substantially circular touch sensitive input devices 216A and 216B, respectively. Each of receivers 200 includes a display 210, a speaker 212, a selection button 214, and an input device 216. Depending on the embodiment, the input devices 216A, 216B may include a capacitive or a resistive input device. For example, a capacitive input device may include multiple capacitive pads, such as 4, 8, 16, 24, or more capacitive pads that extend around the input device 216A, 216B. In one embodiment, a processor of the receiver and/or separate processing logic, is configured to determine the position and possibly a direction and/or speed of movement, of a user finger on the input device 216 in response to data from one or more of the multiple capacitive pads. For example, processing logic may be configured to detect whether the user's finger is moving in a clockwise direction or a counterclockwise direction, and also may determine the speed at which the finger is moving. The determined position and/or direction information may then be used in any number of ways to navigate through menus, options, directions, tutorials, or any other user interface that may be presented on the display 210. For example, actions that a user can control via a circular input device 216 include scrolling, selection of items via a double click (either of the selection button 214 or a portion of the input device 216), forward and backward commands, directional commands (up, down, left, right, diagonals), zooming graphic functions (either scrolling or directional control), scrolling of input values, such as glucose calibration values, pausing, starting and stopping actives (such as instructional videos), etc.

Figure 3:
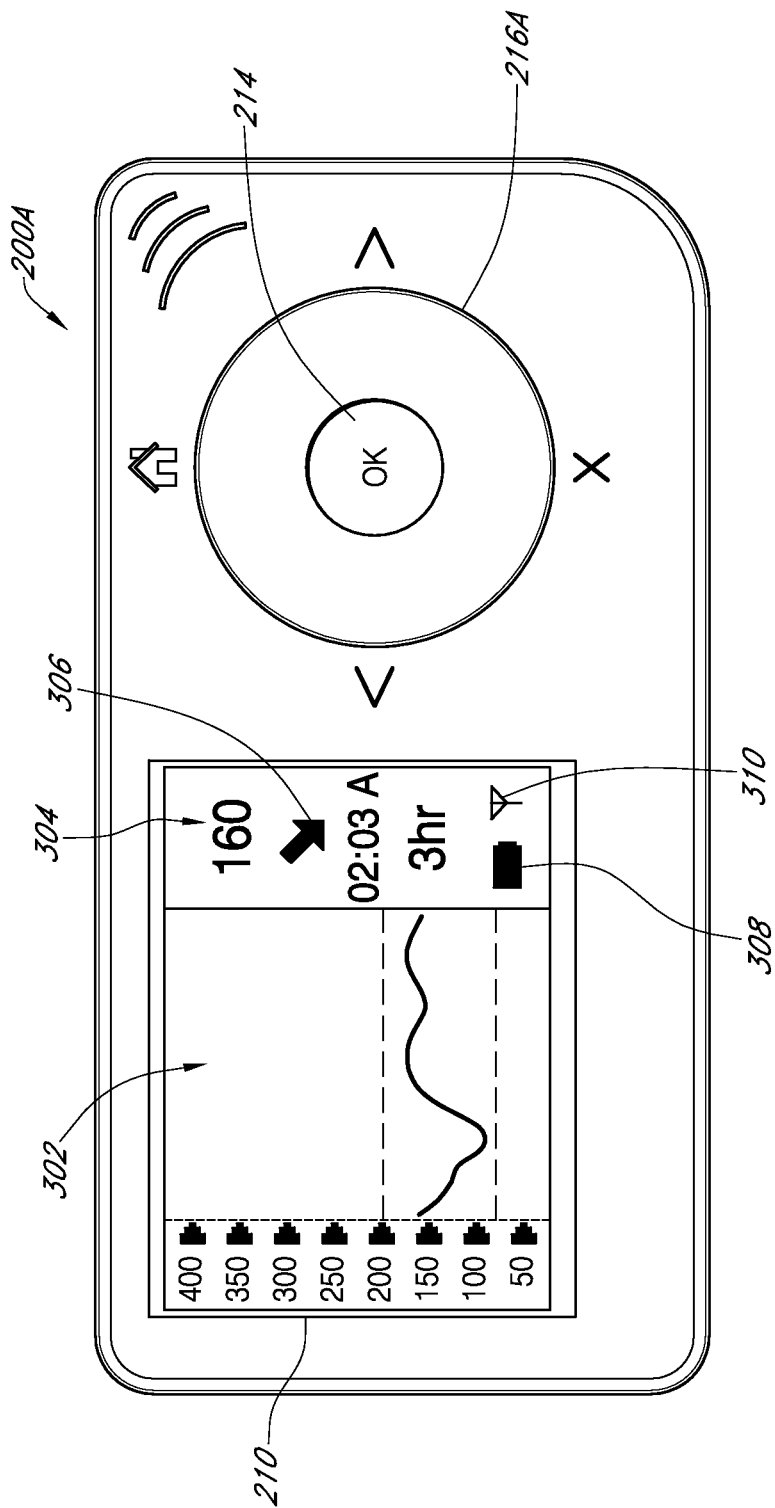
FIG. 3 shows an example of the receiver of FIG. 2A with a glucose chart and other data associated with sensor data and receiver attributes shown on the display.

FIG. 3 is the receiver of FIG. 2A with a glucose chart and other data associated with sensor data and receiver attributes shown on the display 210. In particular, the display 210 includes a three hour glucose chart 302, a current glucose reading 304, a glucose trend indicator 306, a battery life indicator 308, and a signal strength indicator 310. As noted above, the input device 216A may be used in various manners to adjust what is displayed on the display 210. For example, with the three hour glucose chart 302 displayed on the display 210, in one embodiment the time period for the glucose chart may be adjusted by movement of the user's finger on the input device 216A in either a clockwise or counterclockwise direction. For example, if the user moves a finger in the clockwise direction, the time period for the glucose chart 302 on the display 210 may be increased. Additionally, the speed of movement of the user's finger may be detected and used in order to determine an incremental increase in the time period shown on the display 210 (e.g., where faster movement is associated with larger incremental increases in the time period). Similarly, if the user moves a finger in the counterclockwise direction on the input device 216A, a time period for the glucose chart on the display 210 may be decreased, such as at an increment that corresponds to the speed of movement in the counterclockwise direction.

In one embodiment, the selection button 214 may be configured to cycle through various user interfaces on the display screen 210. For example, when the selection button 214 is pressed with the display of FIG. 3, the display may be updated to show a user interface including a menu of setup options. If the selection button 214 is again pressed, the display may be updated to show a user interface including a list of help options. As those of skill in the art will recognize, the types of user interfaces and the order of display of the user interfaces in response to pressing the selection button, or receiving any other input on the input device 216A, may be customized in various manners.

User Interface and Navigation Options

Figure 4:
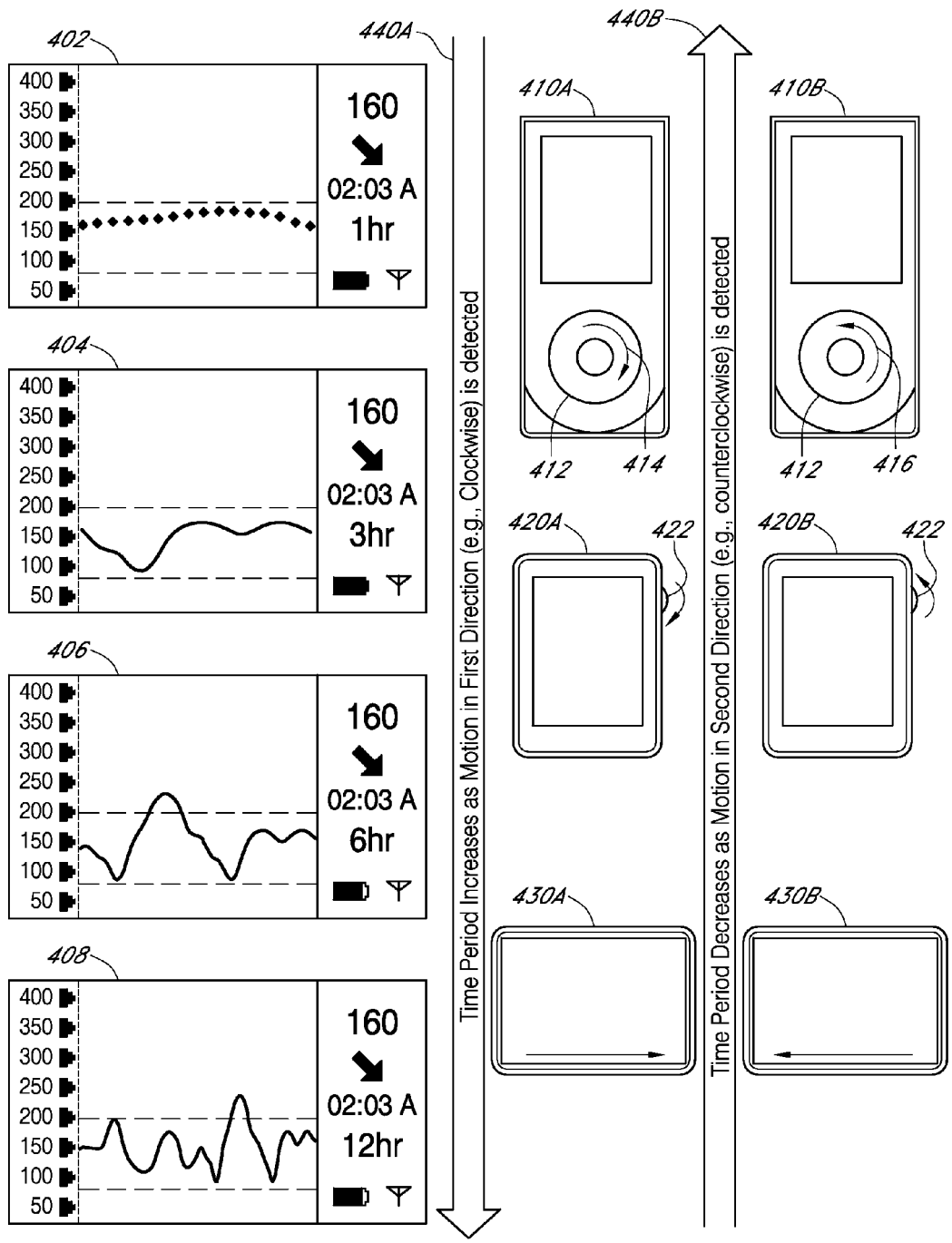
FIG. 4 shows an example illustrating four user interfaces that may be displayed on a receiver at four different points in time.

FIG. 4 illustrates four user interfaces 402, 404, 406, and 408, that may be displayed on a receiver at four different points in time. The user interface 402 includes a one hour glucose chart, while the user interface 404 includes a three hour glucose chart, the user interface 406 includes a six hour glucose chart, and the user interface 408 includes a twelve hour glucose chart. As those of skill in the art will recognize, each of the user interfaces 402, 404, 406, 408 may be desirable for display to a user (e.g., a host, a caregiver, and/or physician) in order to convey various information to the user. For example, a one hour glucose chart (e.g., user interface 402) may be used to track changes in glucose level where a change in the glucose level is expected in response to a recent even, such as after administering an insulin shot to the host. The three hour, six hour, and twelve hour glucose charts convey longer periods of information that can be used to track longer term trends. Additionally, a user may desire to quickly change between glucose charts of various time periods with various predefined user inputs, such as tapping on a touch sensitive input device. For example, one tap on a glucose chart could request a 1-hour chart, 2 taps a 3 hour chart and so forth. In one embodiment, any other time period, such as 24, 48, or 72 hours, or even periods of weeks, months, or years, may be selected for display in the same or similar manner.

FIG. 4 also includes three exemplary receivers 410 (including 410A and 410B), 420 (including 420A and 420B), and 430 (including 430A and 430B). The receiver 410 comprises a touch sensitive scroll wheel 412, such as the input devices 216 described with respect to FIGS. 2A, 2B, and 3. The receiver 420 comprises a mechanical scroll wheel 422 that protrudes slightly from a right side of the receiver 420. In one embodiment, the mechanical scroll wheel 422 rotates in order to provide commands from the user to the software executing on the receiver 420. Depending on the embodiment, the mechanical scroll wheel 422 may also be configured to be depressed in order to provide another input indicator, such as selection of an icon that is highlighted after adjusting a currently selected icon by rotating the mechanical scroll wheel 422. The receiver 430 comprises a touch sensitive display surface, such as a capacitive, resistive, and/or acoustic wave device (e.g., FIG. 1). Each of the receivers 410, 420, 430 advantageously execute software that receives signals from the input devices of the respective receivers indicative of the user's desire to update the time period of the glucose chart currently displayed on the receiver. Thus, each of the receivers 410, 420, and 430 are configured to scroll between user interfaces having different time periods of data displayed on its respective display.

In one embodiment, motion in a first direction on the respective input device of a receiver causes a time period for which glucose data is displayed on the receiver to increase, while motion in a second direction (e.g., a direction opposite to the first direction) causes the time period for which glucose data is displayed on the receiver to decrease. FIG. 4 includes arrows on or near the input devices of the illustrated exemplary receivers, where the arrows indicate a direction of motion on the respective input device. For example, the arrow 414 indicates a clockwise motion on the touch sensitive receiver 410A, while the arrow 416 on the receiver 410B indicates counterclockwise motion on the touch sensitive receiver 410B. The arrow 440A indicates the effect on the time period of the glucose chart displayed on the receiver as the respective receivers detect motion in the directions indicated on receivers 410A, 420A, or 430A. Similarly, the arrow 440B indicates the effect on the time of glucose chart displayed on the receiver as the respective receivers detect motion in the directions indicated on receivers 410B, 420B, and 430B. Accordingly, when clockwise motion on the touch sensitive scroll wheel 412 or by the mechanical scroll wheel 422, or movement from left to right on the touch sensitive display of receiver 430A, are detected, the time period of the glucose chart displayed on the receivers increases. Similarly, when counterclockwise motion on the touch sensitive scroll wheel 412, by the mechanical scroll wheel 422, or movement from right to left on the touch sensitive display of receiver 430B, are detected, the time period of the glucose chart displayed on the receivers decreases. In this way, the user can easily scroll between glucose charts and related data over different time periods. In other embodiments, any other motion may be used in order to indicate changes to the glucose chart time period. Additionally, the input devices of the receivers 410, 420, 430, may be used to change other parameters associated with a particular user interface that is displayed on the display screen. In some embodiments, the input devices of the receivers may be used to navigate through menus, set default options, set alerts, respond to training exercises, access Internet or network resources, scroll through any list of options, such as possible calibration options, and/or to provide any other input to the receivers.

In one embodiment, similar to the sliding, selectable scale on the x-axis, the receiver is also configured to detect motion along the y-axis that may indicate various display changes desired by the user. For example, motion along the y-axis may indicate that the current glucose chart (or other data displayed on the receiver) should be increased or decreased in size (e.g., zoom in or zoom out). For example, in FIG. 1 the user may be able to use touch screen capabilities to slide the glucose scale so that it shows levels between 100 and 200, rather than 50-400 as displayed in FIG. 1. Such a zoom option may provide a higher resolution view of the data and aid in interpreting trends.

In the embodiment of FIG. 1A, the peaks and valleys of the glucose chart are labeled with the actual glucose levels at those peaks and valleys. Similar labeling may occur on any other glucose charts and the labels may include additional information, such as the particular time that the peak or valley was reached. In one embodiment, the user may select a peak or valley (such as by touching the label near a peak or valley on a touch sensitive display) in order to zoom in on that particular portion of the glucose data, display additional information regarding the host at the time of the selected peak or valley, and/or initiate display of any other information. In some embodiments, hovering over, tapping, selecting or expanding any particular time point will cause any or all additional data associated with that time point (e.g., glucose value, reference value, insulin delivery information, insulin on board information, user-initiated events, or other measured parameters associated with that time point) to appear.

In one embodiment, certain receivers, such as receiver having a touch sensitive screen, may include a locking mechanism to prevent changes when accidentally touched.

Figure 5:
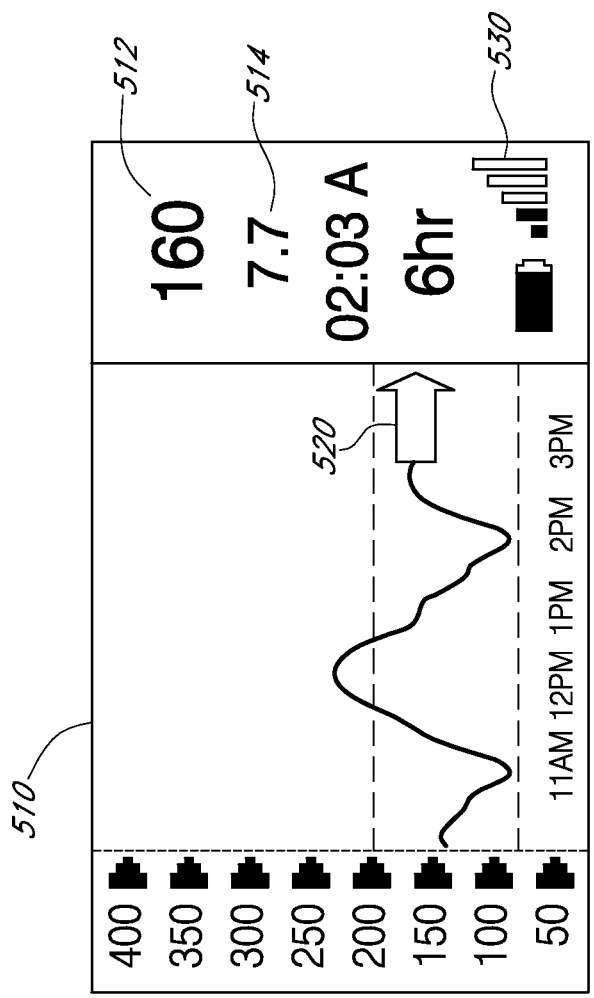
FIG. 5 shows an example of a user interface including a six hour glucose chart as well as a short-term glucose change trend indicator.

FIG. 5 illustrates a user interface 510 including a six hour glucose chart as well as a short-term glucose change trend indicator 520. Depending on the embodiment, the trend indicator 520 may indicate a trend for various time periods. For example, the trend indicator 520 may indicate changes in glucose levels over a 15 minute period. In some embodiments, the trend indicator 520 may be based on changes in glucose levels over a 5, 10, 20, 30, or any other time period. Advantageously, the user interface 510 provides a longer-term indication of glucose level changes (e.g., six hours of glucose data is displayed in the embodiment of FIG. 5), while also showing a current trend based on very recent data that may not be discernible from the longer-term glucose chart. Trend indicators, such as the illustrated arrow, may provide a meaningful resolution of trend information, for example, at least about 10, 15, 20, 25, 30, 40, 50, 60 mg/dL/hour. Additionally, the presentation of the trend indicator preferably provides a unit associated with the rate of change, such as mg/dL/hour or mmol/hour, whereby the user can use the trend indicator for determining their therapeutic decision (e.g., in terms of hours).

In one embodiment, the trend indicator 520 and/or other data of the user interface 510 may change colors according to a status of the trend indicator. For example, if the users glucose level is currently high, but the 15 minute trend indicates a downward movement, the trend indicator may be green (while the actual graph data that exceed the high threshold may be red). Likewise, if the user's glucose level is near a predetermined high and the 15 minute trend indicates upward movement, the trend indicator may be colored red (while the actual graph data remains black or green). Additionally, the glucose level 512 may change color in response to changes in a trend in order to convey trend information without requiring additional display area. In other embodiments, colors, fonts, font formatting, and other display options may be selectively changed in order to convey information associated with sensor data.

In the embodiment of FIG. 5, the user interface 510 also includes an estimated A1C value 514. In one embodiment, software executed by a receiver may be configured to analyze continuous glucose data in order to estimate the user's current A1C value. In one embodiment, a graph showing changes in A1C values of the user over a selected time period, such as one week, two weeks, one month, two months, six months, or any other time period, may also be displayed on a suitably configured receiver. Furthermore, the time period of A1C data displayed on a receiver may be adjusted up or down by simple movements of a user's finger, stylus, or other input device, such as is discussed above with reference to FIG. 4, for example. In some alternative embodiments, the software executed by the receiver is able to process the sensor data to determine average glucose from the sensor data, area under the curve (which can provide a measure of how much exposure a patient has had to glucose) variability (e.g., standard deviation), or the like, and provide the data to the patient directly in real time so they can track their progress right on the receiver through a touch screen process.

A signal strength indicator 530 is also included in the user interface 510. The signal strength indicator 530 graphically indicates a strength of a current communication link between the receiver and a transmitter. In the embodiment of FIG. 5, the indicator 530 includes five horizontal bars, where zero or more of the bars are shaded to indicate a strength of a signal from the transmitter. The particular exemplary indicator 530 of FIG. 5 includes two shaded bars and three unshaded bars, which may indicate that the signal strength is less than half (maybe around ⅖) of a possible signal strength. In this embodiment, if the signal strength is a maximum (e.g., strong enough so that there is no signal lost between the receiver and transmitter), each of the five bars would be shaded. Similarly, in this embodiment if the signal strength is very low (e.g., no recognizable signal from the transmitter is received), none of the five bars would be shaded. In other embodiments, other quantities of bars, as well as different graphical and/or numeric indicia of a signal strength, may be included on a receiver user interface. In one embodiment, a signal strength indicator may be used to locate a lost transmitter. Additionally, a signal strength indicator may be used to allow a user to better troubleshoot transmitter issues, such as by being able to know the strength of the transmitter signal when it is close to the receiver. Additionally or alternatively, the strength indicator can be configured to provide information indicating how recently a data packet (or a glucose value) has been received and/or how many data packets (or glucose values) have been received in a recent time period (and therefore how much glucose information is available and/or a reliability of the glucose trend information, for example).

Figure 5A:
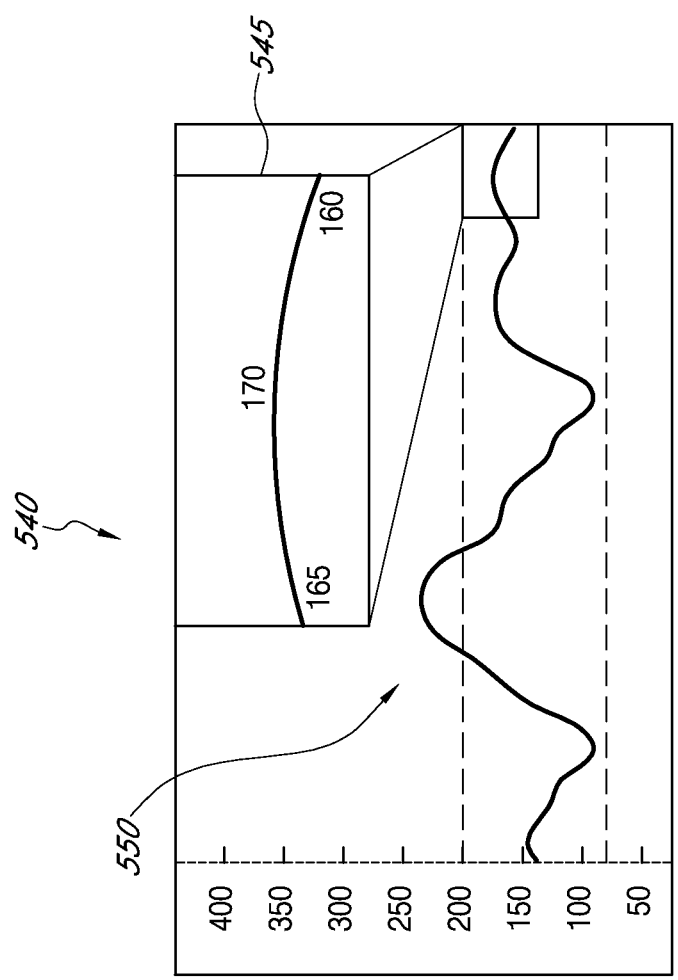
FIG. 5A shows an example of a receiver that depicts a full screen display of a glucose chart that includes a short term chart overlaid on a long term chart.

FIG. 5A illustrates a receiver 540 that depicts a full screen display of a glucose chart that includes a short term chart 545 overlaid on the long term chart 550. Thus, the user can view details of the most current glucose data as illustrated in FIG. 5A, or may view any other time period in the short term chart 545 by providing appropriate inputs to the receiver 540. For example, tap a portion of the glucose chart of touch sensitive display or turning a mechanical or touch sensitive wheel may indicate different time periods for display in the short term chart 545. The short term chart 550 may be displayed near the corresponding position of the same data on the long term chart 550, in any unused area of the long term chart 550, and/or in a separate window that may be displayed on the receiver 540.

Figure 6A:
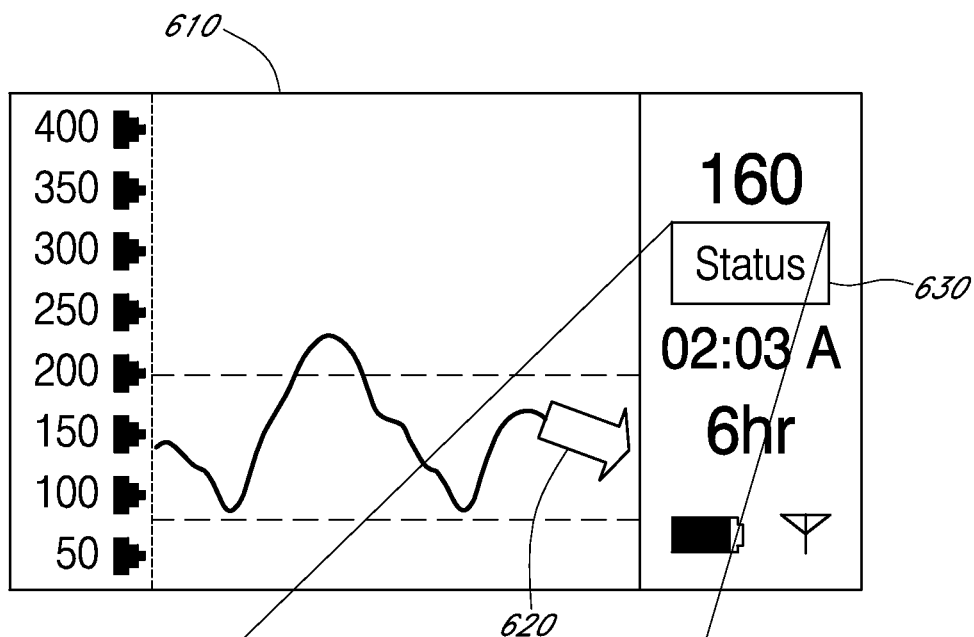
FIG. 6A shows an example of a user interface that includes a trend indicator indicating a trend in glucose level changes over a different time period than is displayed on a chart.

FIG. 6A illustrates a user interface 610 that also includes a trend indicator 620 indicating a trend in glucose level changes over a different time period than is displayed on the chart of user interface 610. As noted above, the trend indicator 620 may be configured to indicate a trend over any available time period, either shorter or longer than the time period on which the current glucose chart is based, such that data from two different time periods is concurrently displayed on the user interface 610. The user interface 610 also has a status window 630 that indicates additional status information associated with the receiver or the sensor, for example. In one embodiment, the status window 630 includes an indicator of the remaining useful life of the sensor from which the receiver is currently receiving glucose data. In one embodiment, the status window 630 includes an indicator of an estimated time until a next calibration is suggested. In other embodiments, the status window 630 may include any other information available to the receiver. The status window can provide information such as time since sensor insertion, confidence level of sensor data, trend information and/or predicted information, amount of time the sensor is/was on/off during a sensor session, and/or various other data associated with the receiver, sensor, and/or host.

Figure 6B:
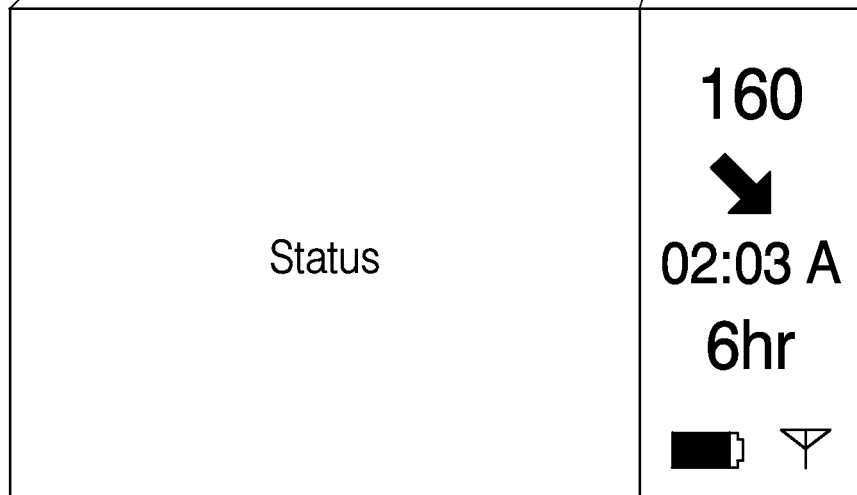
FIG. 6B shows an example of a user interface that may be displayed on a receiver in response to the user selecting a status window.

In the embodiment of FIG. 6A, the status window 630 may be selected, such as by touching the status window 630 on a touch sensitive display of a receiver, or selecting the status window 630 using other input devices, in order to expand the display of status information, and to possibly include additional status information. FIG. 6B illustrates an exemplary user interface 640 that may be displayed on a receiver in response to the user selecting the status window 630 (FIG. 6A).

FIG. 7 illustrates a user interface 710 including a glucose chart for a 3 hour time period and a navigation bar 720 that shows glucose data over a longer period. In the example of FIG. 7, the navigation bar 720 illustrates glucose data for a 24 hour time period. In this embodiment, the time period of glucose data displayed in the window 712 may be adjusted by moving the slider 722 to the left (e.g., in order to increase the time period of data displayed in the window 712) or to the right (e.g., in order to decrease the time period of data displayed in the window 712). Depending on the hardware of the receiver, the slider 722 may be moved in response to various user inputs. For a touch sensitive receiver, such as the receiver 100, for example, a user may touch and drag the slider 722 in order to adjust the time period for which data is displayed in the window 712. In one embodiment, as the slider is moved the total time period for which data is displayed in the navigation bar 720 also changes. Thus, in one embodiment when the slider 722 is moved to the left, not only does the time period for which data is displayed in the window 712 increase, but the total time period for which data is displayed in the navigation bar 720 also increases. For example, with reference to the specific user interface 710 of FIG. 7, if the slider 722 is moved to the left so that 24 hours of sensor data is displayed in the window 712, the navigation bar 720 may be updated to include data from a 48 hour period, rather than the 24 hours of data illustrated in FIG. 7.

In the embodiment of FIG. 7, the user interface 710 also includes a remaining sensor life indicator 714. In this embodiment, the dark portion 715 of the indicator 714 illustrates a portion of the sensor life that remains (relative to the entire length of the rectangular icon). In this embodiment, the indicator 714 also indicates an estimated time period for which the current sensor is suitable for use. Suitability may be based on expiration of the glucose sensor, accuracy of the glucose sensor data, noise associated with the glucose sensor data, time since sensor insertion, an algorithmic determination of sensor end-of-life, or the like. In particular, the indicator 714 illustrates that the current sensor is suitable for use for another two days. Depending on the embodiment, the time estimate of a remaining sensor life indicator may be only displayed when sensor life is below a predetermined threshold, such as one week, two days, or one day, for example. Depending on embodiment, sensor life indicators such as the indicator 714 of FIG. 7 may be included in various other user interfaces that are displayed on receivers, such as in the status window 630 of FIGS. 6A and 6B.

In the embodiment of FIG. 7, the glucose chart displayed in window 712 also includes event tags that indicate when particular events occurred. In this particular embodiment, the tags include a food tag 716 and an insulin tag 718, which indicate specific times at which the indicated events occurred. In other embodiments, any number of indicators may be available for tracking events, such as exercise, sleep, ill, and any other events that might be interesting to the user and/or others that view the user's glucose data (e.g., the users physician). In one embodiment, the event indicators move as the selected time period is changed so that they continue to point to the appropriate position of the chart. Event indicators may be added to the glucose chart (and associated with the selected event time for later use) in response to a predefined user input, such as touch of a portion of the glucose chart in a touch sensitive display, for example. In one embodiment, the event indicators may be selected, such as by touching the icons displayed on a touch sensitive receiver, in order to initiate display of further information regarding the selected event. Depending on embodiment, the additional information regarding the event may be displayed in a pop-up type window that covers a portion of the user interface 710, or a separate window that replaces the user interface 710, or possibly the window 712.

Figure 8:
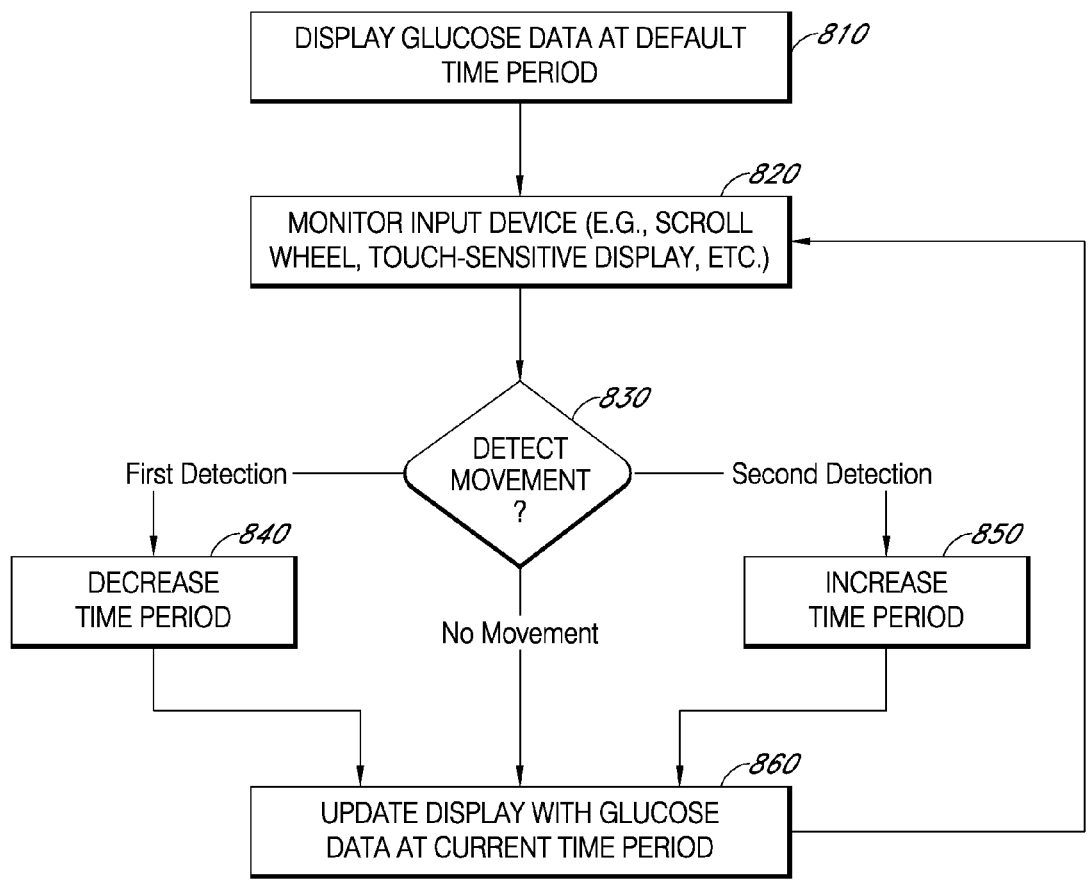
FIG. 8 shows an example of a flowchart illustrating one embodiment of a method of monitoring an input device in order to adjust a time period of sensor data that is displayed on the device.

FIG. 8 is a flowchart illustrating one embodiment of a method of monitoring an input device in order to adjust a time period of sensor data that is displayed on the device. For example, the method of FIG. 8 may be used in order to adjust the time period for a glucose chart that is displayed on a receiver that receives continuous glucose data from a continuous analyte sensor. Although FIG. 8 is described with respect to adjusting time periods associated with glucose data, the method of FIG. 8 may be used to adjust any other time periods, such as the time period of sensor data used in a chart illustrating historical estimated and/or actual A1C values. Depending on the embodiment, the method of FIG. 8 may include fewer or additional blocks and blocks may be performed in a different order than is illustrated in FIG. 8.

Beginning in block 810, sensor data for a default time period is displayed on the receiver. In one embodiment, the default time period is preset by a manufacturer and may be adjusted by the user to customize the default time period. The glucose data may be displayed in various formats, such as the line graphs that are included in many of the figures, other types of graphs or charts, and/or raw or summarized sensor data.

Moving to block 820, the receiver monitors signals received from the respective input device(s) in order to determine if movement on one or more of the input devices has been detected. Depending on embodiment, input devices may include one or more touch sensitive surfaces, such as a capacitive, resistive, and/or acoustic wave devices, a scroll wheel, either touch sensitive or mechanical, and/or any other available input device.

Next, in block 830, the receiver determines if movement has been detected on one or more of the receiver input devices. If movement in a first direction has been detected, the method moves to block 840 where the time period for which sensor data is displayed is decreased. Alternatively, if movement in a second direction is detected, the method moves to block 850 where the time period for which sensor data is displayed is increased. In one embodiment, the decrease (e.g., block 840) or increase (e.g., block 850) occurs at a predetermined increment. In another embodiment, the decrease (or increase) in the time period change is adjusted based on a speed and/or acceleration of the detected movement, such that a fast movement results in a decrease (or increase) in the time period at a greater interval than a slow movement would cause. In block 830, if no movement is detected, the method continues to block 860 where the display is updated to illustrate sensor data for the current time period. Accordingly, if the time period has been adjusted at blocks 840 or 850, the display will be updated to include additional or less (depending on whether the time period has increased or decreased) sensor information. With the time period for the sensor data updated in block 860, the method returns to block 820 where the input device(s) of the receiver are monitored for additional movements that may indicate further changes to the time period.

Receiver Modes

Figure 9:
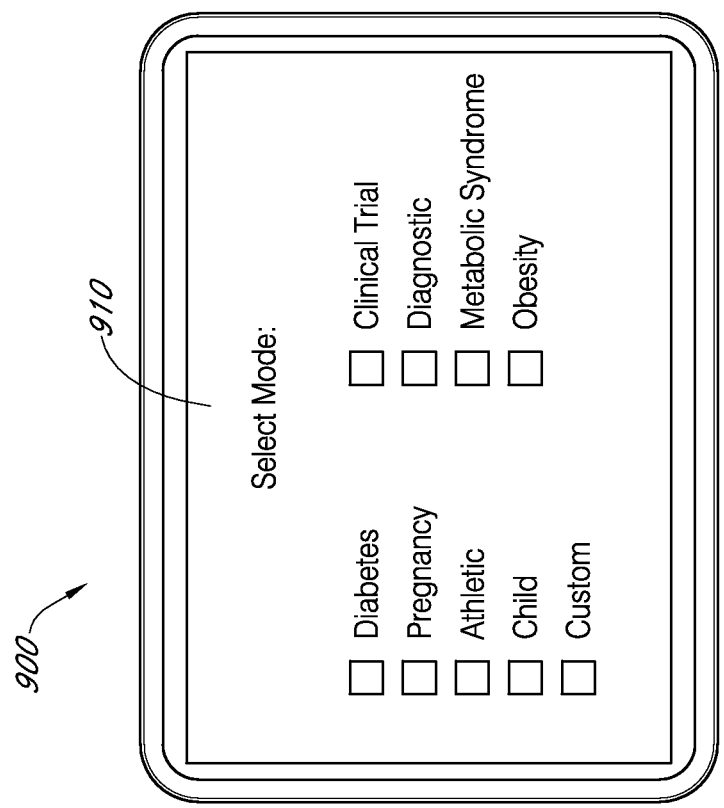
FIG. 9 shows an example of a touch sensitive receiver displaying a user interface that allows a user to select an operation mode.

FIG. 9 illustrates a touch sensitive receiver 900 displaying a user interface 910 that allows the user to select an operation mode. In one embodiment, a mode selection interface, such as the user interface 910, may be presented to a user upon initial setup of the receiver and/or at any other time when the user wishes to adjust an operational mode. Similar interfaces may be presented to users on any other type of receiver, such as the receivers illustrated in FIG. 4. Advantageously, each mode may have different menu options, sensor readings, graph types, default graph time periods, alert algorithms, and/or other receiver settings. For example, if a pregnancy mode is selected, sensor data may be received from a body temperature and/or pulse rate sensor, while the diabetic mode receives data from a transcutaneous glucose sensor. Furthermore, the types of information displayed to a user in the different modes may vary. For example, the athletic mode may receive data from a heart rate and/or blood pressure sensor and charts may be generated to indicate the users heart rate and/or blood pressure over various time periods, which may be adjusted according to the method described in FIG. 8, for example.

Modes may be provided to allow a user to customize display and alert preferences based on a status of the user and/or a status of the receiving display device. For example, different user-selectable modes based on the status of a user may include one or more of resting, exercise, do not disturb, silent, loud, soft, illness, menstruation, mealtime, snooze, day, night, hyperglycemica, hypoglycemia, clinical risk, and the like. These modes may be selected by the user at anytime and may be selected to be activated and deactivated according to a schedule. For example, a sleep mode may be selected such that it is activated from 10 pm to 7 am each night or a do not disturb mode that may be selected such that it is activated from 1 pm to 4 pm Monday through Friday. In another embodiment, a selected mode may be associated with a timer such that after an indicated time period, the mode is automatically changed back to a default mode. For example, a user may select an exercise mode when entering a gym for a one hour training session and may associate a sixty minute timer so that the default mode is activated automatically after the workout is complete.

The selected mode may indicate changes in how glucose data is displayed based on the display/response preferences specified for each mode. For example, a mealtime mode may adjust a time period for displaying glucose data on a glucose chart by shortening the time period displayed to show a higher resolution of changes in glucose levels while the mode is selected. Furthermore, when a person is exercising, his/her glucose levels may increase or decrease in trends that would be abnormal under any other circumstances; by selecting an appropriate mode, additional information specially applicable to exercise conditions may be displayed and formatting may be adjusted.

Additionally, alerts associated with respective modes may vary in order to detect sensor data that is of interest to the user that has selected that particular mode. For example, selection of the diabetes mode may select alerts and corresponding alert conditions associated with high and low blood glucose thresholds. However, these same alerts may not be interesting to a woman that is going through a high risk pregnancy and wishes to track certain of her vital signs. Similarly, an athlete that selects the athletic mode may be interested in receiving alerts indicating that the athletes heart rate exceeds a predetermined (e.g., user defined) threshold. Additionally, alerts for a child with diabetes may be at different levels than would be customary for an adult with diabetes, and changes in a child's blood glucose levels over time may be less or more indicative of changes that should trigger an alert. Accordingly, the alert conditions associated with different modes may vary. Furthermore, the delivery method for triggered alerts may vary according to a selected mode, such that an alert for a child that has reached a blood glucose level near hypoglycemia may be transmitted to a caregiver of the child, while a similar alert for an adult that may be displayed only on the adults receiver. Thus, each of the modes may include custom alerts and corresponding alert conditions, as well as delivery options, which may be further customized by the particular user to meet the user's needs.

In one embodiment, the selected mode may affect which alerts are triggered such that certain sensor data might trigger an alert when the user has selected a first mode, but would not trigger an alert when the host has selected a second mode. For example, an alert that may be triggered when a user has selected a day mode, may not be triggered when a user has selected a night mode. Furthermore, the length, volume or type of alert may change based on the selected mode. For example, when a soft mode is selected, the volume of alerts are automatically reduced, while in a silent mode, a vibration alert is used in place of an audible alert.

In one embodiment, the algorithms that are used to analyze sensor data may change based on a selected mode. For example, a child with diabetes may select the child mode in order to initiate monitoring of blood glucose levels of the child and to provide appropriate alerts. However, the blood glucose level of the child may be calculated using a different algorithm than might be used for an adult (using the standard diabetes mode).

In one embodiment, each of the available modes is associated with predetermined default sensor information, menu options, charts and/or report types, alert criteria, and/or data analysis algorithms, which may be adjusted by a particular user to meet the users specific needs. Additionally, a user may select a custom mode in order to define custom settings for any of the above noted attributes.

In other embodiments, other features of the receiver software may be customized based on a selected mode. For example, different icons may be associated with different modes. For example, an athletic mode may include icons that illustrate an athlete in various positions, while the child mode may have default icons that indicate static or animated cartoon characters. In one embodiment, certain modes require different setup information and, thus, may be associated with different information requests as part of a mode setup routine (see FIG. 10 for an exemplary setup routine). For example, a mode that is associated with multiple sensors may include additional requests for sensor information as part of a mode setup routine. In some embodiments, different modes are associated with different noise filtering algorithms. For example, in the child mode, the noise filtering software may provide additional filtering as compared to the noise filtering provided when in the diabetes mode.

Figure 10:
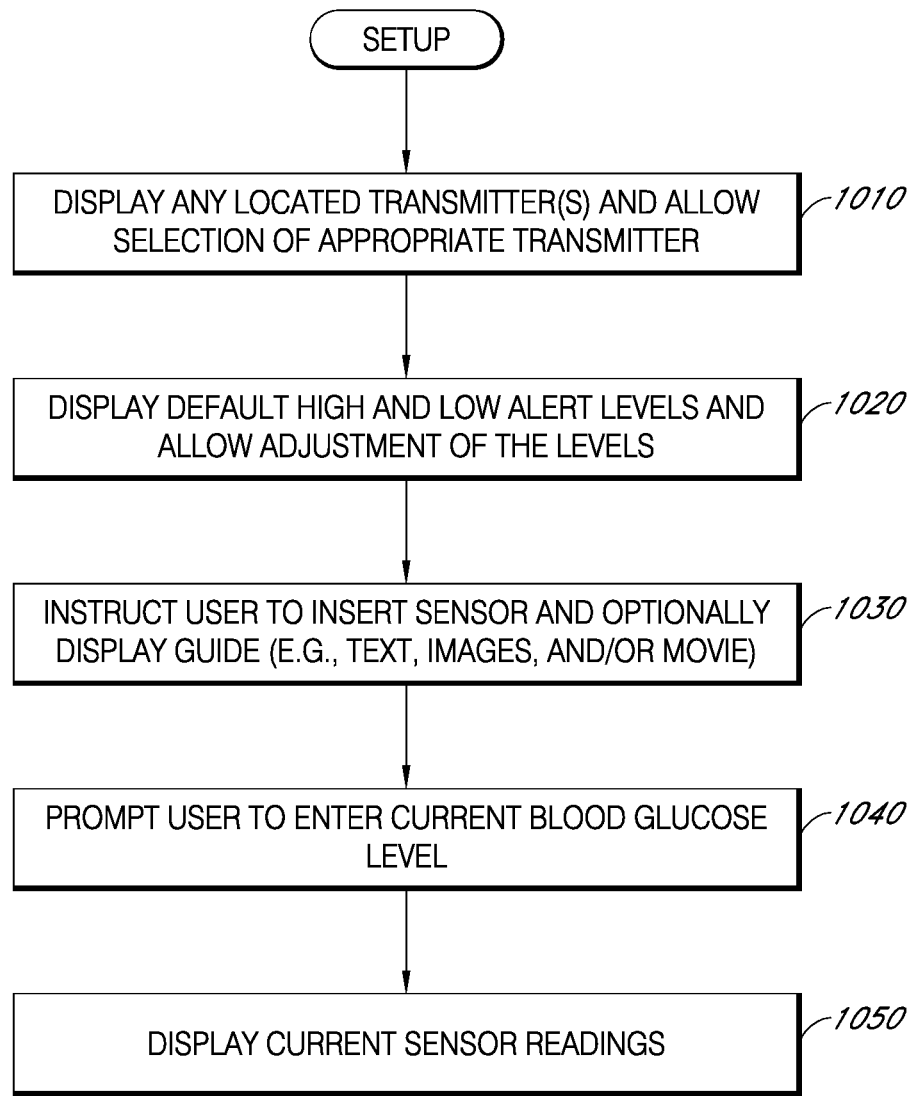
FIG. 10 shows an example of a flowchart illustrating an exemplary start up process that guides a user through an initial set-up of a receiver.

FIG. 10 is a flowchart illustrating an exemplary start up process that guides the user through the initial set-up of the receiver. A method similar to that of FIG. 10 may also be initiated by receiver software in response to changing a mode of the receiver, such as is discussed above with reference to FIG. 9. Thus, the method of FIG. 10 may be considered a startup process and/or a mode setup routine. Depending on the embodiment, the method of FIG. 10 may include fewer or additional blocks and/or the blocks may be performed in a different order than is illustrated. For example, any other number of requests for information and/or displays of additional information may be included as part of a startup process.

Beginning in block 1010, the receiver displays identifiers of any located transmitters and allows the user to select one or more appropriate transmitters for communication with the receiver. In one embodiment, the receiver automatically detects any sensors within range of the receiver when the method of FIG. 10 is initiated (e.g., when a receiver is initially set up or when a mode of the receiver has been changed). In such an embodiment, the user may be provided with a list of detected sensors and be allowed to select one or more of the sensors from which the receiver should receive and/or request data. In an embodiment where a receiver includes a touch sensitive display, sensors may be selected by touching icons (and/or text) representing various located sensors that are depicted on the display. In response to selection of one or more sensors, the receiver may request further information from the user regarding how the sensor data should be used by the receiver.

Next, in block 1020, the receiver displays the default high and low alert levels for sensor data received from the sensor and/or derived from the sensor data. For example, if the method of FIG. 10 is executed in response to a user selecting the child diabetes mode (see FIG. 9, for example), the receiver may display a default hypoglycemia alert level and a default hyperglycemia alert level (as well as any number of other alerts). In one embodiment, the user is provided an opportunity to adjust the default alert levels and/or add additional alerts at this stage of the method. For example, a default hypoglycemia alert level may be adjusted by swiping a finger across a touch sensitive screen, rotating a mechanical scroll wheel, or moving in a clockwise or counterclockwise motion on a circular touch sensitive input device. Alert delivery options may also be displayed to the user and the user may be allowed to adjust the delivery options.

Moving to block 1030, the user is instructed to insert and/or place one or more sensors on the appropriate anatomical positions, if not already so positioned. In one embodiment, the receiver displays text, images, and/or video illustrating where and how selected sensors are to be optimally positioned.

In block 1040, the user is prompted to enter current calibration information, such as a current blood glucose level when a diabetes mode, or any other mode that tracks blood glucose level, has been selected. Depending on the selected mode, the information requested in block 1040 may vary. For example, calibration information regarding a blood pressure sensor may be requested in order to properly calibrate a blood pressure sensor from which the receiver receives data.

In block 1050, the receiver initiates tracking of the indicated sensor data and monitoring of the indicated alerts according to the default levels that were displayed to the user during the setup routine, or using user-defined levels that were received by the user during the setup routine. The receiver may then display the current sensor readings on the receiver according to the determine default and/or user preferences. The initial display on the receiver may vary from one embodiment to another.

Proximity or Accelerometer Sensor

The screen size of the receiver's display may limit the amount of historical glucose data that may be shown on the display at one time. For example, glucose data indicating a trend in glucose level changes over a specified time period may include trend data for a span of several months; however, the receiver may show one week of data on the display at one time. To allow a user another method for changing the time period displayed on the receiver (e.g., which seven days of data are displayed), a sensor may be included within the receiver which provides data about the receiver's relative position in space. For example, a gyroscope, proximity sensor, velocity sensor, accelerometer, or the like may be included within the receiver to provide position data. Data from the sensor allows the receiver to detect the movement of the receiver as controlled by the user and may be used to change the data range displayed on the receiver based on how the user physically moves the device. For example, the display may show a portion of a glucose trend data set which depends on the relative position of the receiver in space. By holding the receiver in the air, the user may move the receiver to the left to go back in time, or the user may move the receiver to the right to move forward in time. Thus, using receiver position input may allow a user to "scroll" through trend data as a user moves the device. The receiver may also include a "lock" button in order to lock the data displayed on the screen so as to allow movement of the receiver without changing the current data range on the display.

Data Integrity

A user may wish to view and respond to glucose data using multiple remote viewers. Preserving data integrity when transmitting and receiving glucose data may be important to ensure that a user makes correct therapeutic decisions based on accurately transmitted glucose values. For example, a glucose value of 398 mg/dl may be transmitted by a base station to a remote viewer as string of numbers "398." As the string is transmitted, there is a possibility that, for example, the "3" character would be dropped. In this case, the remote viewer may simply display "98 mg/dL" which may create a significant medical risk that a user will respond to the incorrect value in a way that would be harmful. To avoid displaying incorrect glucose values in such a scenario, a validated transmitting device may instead send a screen shot or image of the glucose data. For example, the glucose data may be sent as a low resolution image, a compressed image or a data format such as a jpg, pdf, png or the like. In this manner, the risk of displaying an incorrect value invoking a harmful therapeutic decision is reduced.

Current Time Display

As shown in FIG. 1, the receiver may show the current time on the display, such as in the space next to the glucose chart. To save space on the display, the current time value may be repositioned and displayed instead in the glucose chart at the end of the time on the time axis. In this way, space may be saved on the screen. Furthermore, displaying the current time at the end of the time axis may provide an intuitive reference value for aiding a user in interpreting the glucose chart.

Background Displays

A variety of mobile communication devices, such as a cell phones, may be configured as primary or secondary devices for viewing glucose data. On some such devices, a user performs a series of operations before glucose data is displayed such as activating or "waking" a device, unlocking a device, logging in using a passcode, and browsing for and launching an application. This may reduce the device's ease of use for providing glucose information which is easily accessible to users.

Figure 11A:
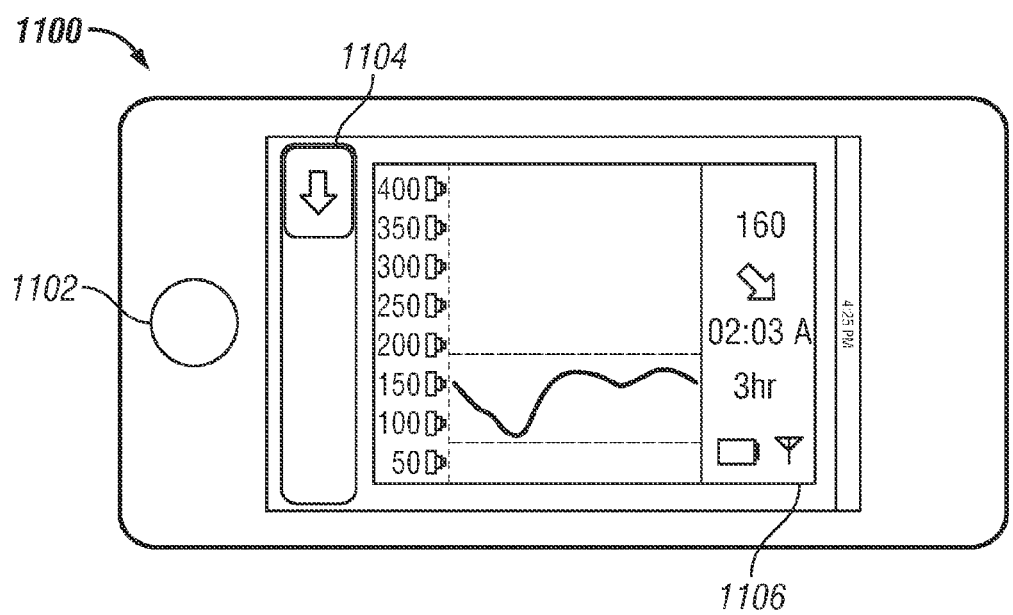
FIGS. 11A and 11B show an example of a device with a background display showing glucose information.
Figure 11B:
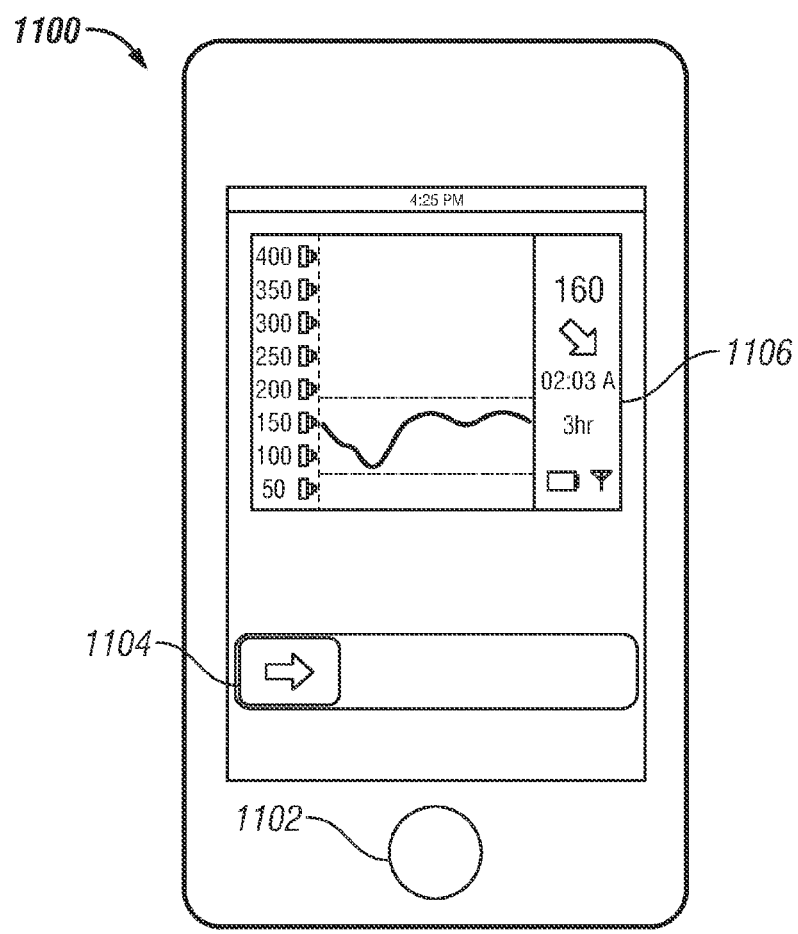

To allow glucose data to be more easily accessible, glucose information may be displayed on a background display for a device and the glucose information may be continually updated by an application running in the background. FIG. 11A shows an example of a device 1100 with a background display 1106 showing glucose information. The device 1100 may include a button 1102 that may be used to wake up the device when the device is in a sleep mode. The glucose information may be displayed on the background display 1106 when the user presses the button 1102 to wake up the device. Furthermore, the background display 1106 showing glucose information may be displayed before the user performs operations such as an unlock operation by using an unlock mechanism 1104. Thus, in one aspect, displaying the data in a background screen may allow a user to view glucose information by simply waking up the device. In another aspect, glucose data may be displayed in the background without requiring a user to enter a passcode or launch an application. If a user wishes to be provided with additional information about the glucose data, an application launch button may also be provided on the display. In another embodiment, a button or a specially defined passcode or "quick code" that may be entered by the user may also be provided to allow for an additional method for displaying glucose information on the device quickly. Examples of devices that may take advantage of displaying glucose data in a background display may include but are not limited to cell phones, insulin pumps, automobile displays, computers, or other electronic systems where user information is displayed. In FIG. 11A, the background display 1106 showing glucose information is displayed using a landscape orientation. FIG. 11B shows an example of a device 1100 with a background display 1106 showing glucose information using a portrait orientation.

Continuous Alert Profiles

Under certain circumstances, a user may miss an alarm and may need to be warned several times of a hypoglycemic glucose condition. A profile may be provided, that when chosen by a user, repeatedly alerts a user of a hypoglycemic condition until either the user acknowledges the alert, or the estimated glucose value reaches a safe range. This profile may be applied to several different types of alarms, such as for example, a fixed low alarm.

Alarm Tune Generation

An alert system may use several different alarm tunes, or musical tone sequences, to aid a user in distinguishing between different alarms. When individual alarm tunes are stored as separate media files, such as a wav audio file, a large amount of the receiver's memory is consumed. For example, storing a thirty second sound file, corresponding to one alarm tune could require one megabyte of memory. Alternatively, rather than storing individual alarm tunes as separate media files, individual alarm tunes may be generated at the time they are needed by using a small set of tones stored in memory. In another embodiment, the tones themselves may be generated at the time an alarm is triggered without a need to store tones in memory. As a result, only a small portion of memory (e.g., flash memory) is used for storing alarm tunes, and at any time, only one alarm tune currently being played may needed to be stored in active memory (e.g., SDRAM). In addition, a large variety of different alarm tunes may be generated without requiring each separate alarm tune to be stored individually.

Indicator Lights

As described herein, continuous glucose monitor systems gather and display glucose information in real time to users and a receiver may display current glucose information, trend arrows and trend graphs. A receiver may also have a series of alarms which are triggered when a glucose value goes above or below preset alarm limits. Predictive algorithms may also be provided which use historical glucose data to predict a future glucose value such as what a glucose value might be in ten, thirty, or sixty minutes. In response to the predicted values, alarms may be triggered according to preset alarm limits.

Figure 12:
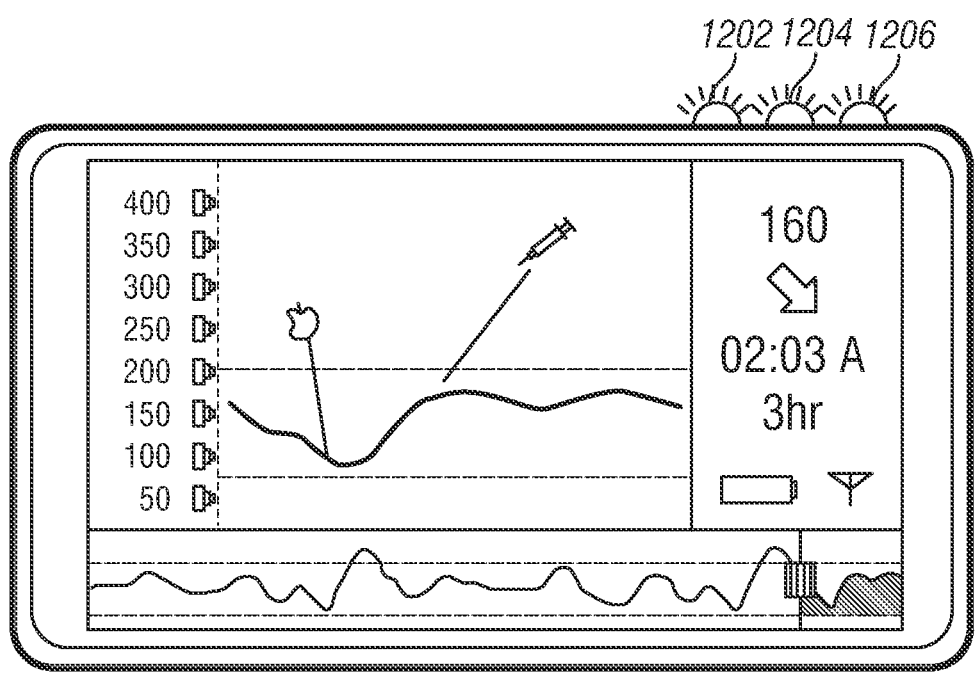
FIG. 12 shows an example of a display device including indicator lights for indicating information about the status of glucose levels or according to other system status information.

In many current display devices, in order to obtain both current and predicted glucose values, a user may be required to perform a series of actions to view trend graphs or glucose meters on the receiver's display, such as activating a display by pushing a button. To provide a user with an additional method for gaining information about current glucose data or a system status, an indicator light or series of indicator lights may be provided on the receiver. FIG. 12 shows an example of a display device 100 including indicator lights 1202, 1204, 1206. The indicator lights 1202, 1204, 1206 may be included on top of the side of the device 100. An indicator light 1202 may display a color according to the status of the patient's glucose levels or according to other system status information. In one embodiment the indicator light 1202 is a green color, while another indicator light 1204 is a yellow color, while yet another indicator light 1206 is a red color. For example, an indicator light 1202 may be a solid green color if a measured glucose value is in a target range and a predicted glucose value is also in the target range. The indicator light 1202 may change to a solid yellow color if the predicted glucose range is outside the target range but the current glucose value is inside the target range. The indicator light 1202 may change to a solid red color if the current glucose value and the predicted glucose value are outside of the target range.

An indicator light 1202 may be configured to indicate further information such as the status of a glucose sensor (e.g., either functioning or blanketed data), a status of a glucose value when a receiver is in silent mode (e.g., as an alternative to providing an alarm), a status of a predicted glucose value, or a status of an insulin pump. In addition, an indicator light 1202 may indicate the distance between a current glucose value and a target range, or be used for indicating a hypoglycemia condition versus a hyperglycemia condition. An indicator light 1202 may indicate different types of information by using multiple colors, by using blinking lights, by varying light intensity, or by combining a series of indicator lights whose illuminated length communicates certain information. The indicator lights 1202, 1204, 1206 may be light emitting diodes (LEDs) for example. Indicator lights 1202, 1204, 1206 may be placed on the edge or side of the receiver to allow a light to be easily observed. For example, an indicator may be placed so that it may be observed when the receiver is placed on any surface or if the receiver is pulled partially out of a pocket, such as on the top of the side of the device. At least one benefit provided by using indicator lights as described includes providing an additional method for gaining information about a glucose and/or sensor status without requiring the user to view information shown on a display. Indicator lights may be placed on receivers such as cell phones, insulin pumps, transmitters, automobile displays, computers, or any other electronic device.

Light Attachment

Figure 13A:
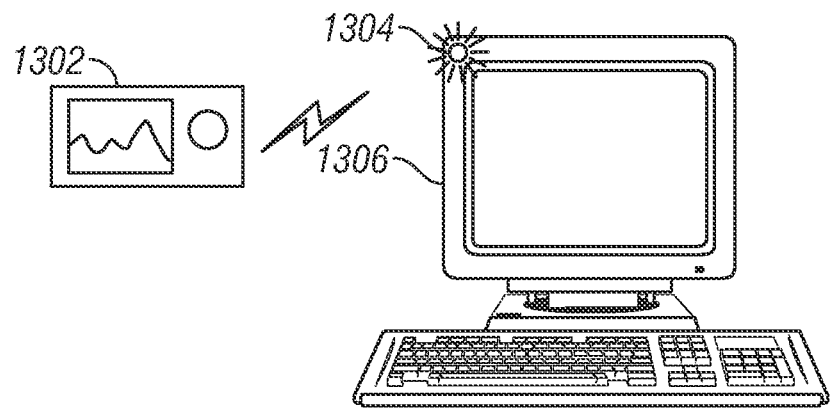
FIG. 13A shows an example of a light indicator device attached to the edge of a computer for indicating glucose information.

Light indicators may also be placed in various locations to aid a user to quickly be able to determine the status of a current glucose level or a trend in glucose data. The light indicators and a housing may be connected wirelessly to a primary receiver. For example, a small device may be provided which includes an LED light, a wireless receiver, and a battery along with a housing. This device may be placed, for example, on the edge of a computer, a rear view mirror of a car, or on the edge of a television using adhesive or other attaching means. FIG. 13A shows an example of a light indicator device 1304 that is attached to the edge of a computer 1306. The light indicator device 1304 receives wireless information from a primary receiver 1302 for indicating the status of a current glucose level or trend in glucose data. For example, if a user's glucose level begins to fall, an LED light of the light indicator device 1304 may be a solid red color. The intensity of the LED might increase as the glucose level falls lower and lower. If the glucose level reaches a low threshold, the red light may begin to blink. Conversely, as a person's glucose level rises, the LED light may change to a solid blue color and may increase in intensity as glucose levels becomes higher and higher. If the glucose level reaches a high glucose threshold, the blue light may begin to blink.

Figure 13B:
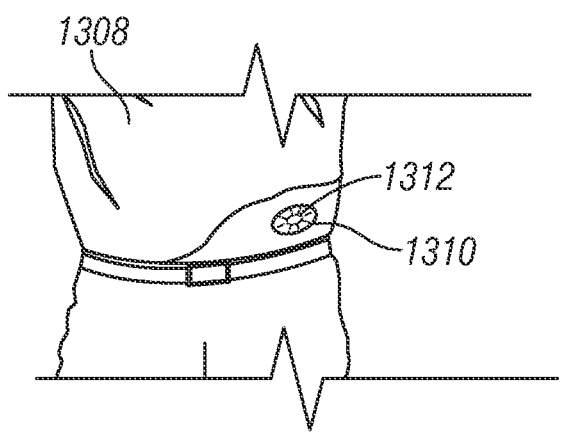
FIG. 13B shows an example of a light indicator device attached to a sensor/transmitter device worn on a person's body for indicating glucose information.

In another embodiment, a light indicator may be embedded within a sensor/transmitter that is worn on a persons' body. FIG. 13B shows an example of a light indicator device 1312 attached to a sensor/transmitter device 1310 worn on a person's body 1308. In this embodiment, a separate wireless receiver and battery would not be necessary as the device 1312 may use the battery and receive data directly from the sensor/transmitter 1310. Furthermore a primary receiver would not be necessary to transmit information to the light indicator device 1312. The light indicator device 1312 could be integrated as part of the sensor/transmitter device 1310, or it may be attached (e.g., snapped) onto the sensor/transmitter device 1310. By allowing a light indicator device to be attached, a light indicator device would be capable of being removed if desired and separately sold.

Differentiated Display of Glucose Units

Figure 14:
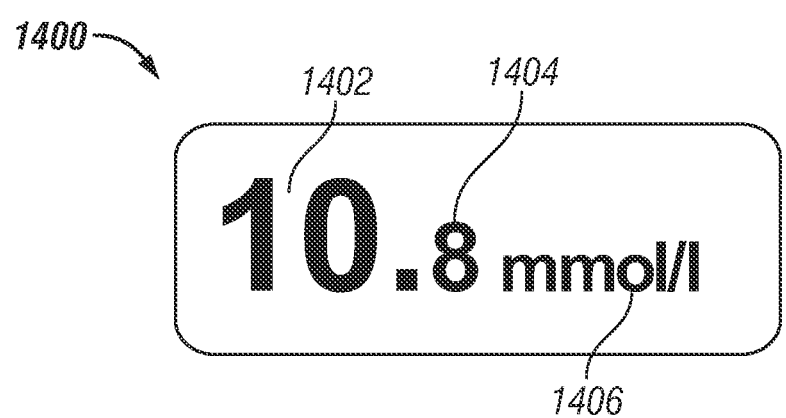
FIG. 14 shows an example of a portion of a user interface displaying a glucose level reading from a sensor.

When displaying glucose values, different units may be used depending on the source of the glucose information or the type of device that is being used to display the information. For example, glucose units may be displayed as milligrams per deciliter (mg/dl) or millimoles per liter (mmol/l) depending on whether the device is a receiver, an insulin pump, an integrated pump/receiver device, or a glucose meter. To prevent user confusion between different glucose units, the graphical representation of the digits may be configured to allow differentiation between different units. For example, when representing a value using mmol/l units, decimal digits may be reduced in size as compared to the integer digits. This is shown for example, in FIG. 14 which shows a glucose value 1400 with an integer digit 1402, a decimal digit 1404 and a unit 1406. As shown, the decimal digit 1404 is reduced in size enough to be easily distinguished from the integer digit 1402, while the unit 1406 is reduced in size as compared to the integer digit 1404 and the decimal digit 1406. In another embodiment, the glucose values may be displayed by using different colors or by using hyphenation between the digits. This may allow a user to more easily distinguish between different glucose units in order to prevent a user from making a therapeutic decision based on a mistaken reading. As one example, this method may prevent a user from reading the value 10.8 mmol/l as 108 mg/dl.

Icons for Displaying Real-Time Data

Receivers may use various icons to indicate and display glucose levels. For example, when a low alarm is triggered, a "low glucose" icon may be displayed on the receiver. To allow a user to receive additional information about glucose levels, the icon displayed may additionally provide alert symbols and/or real-time data. For example, a "low-glucose" icon may include an arrow pointing down along with the actual glucose level from a sensor. Other alert symbols or data may also be included.

Automatic Adjustment of Display Settings to Attract User Attention

As a user's real time glucose levels increase or decrease, the cognition or awareness of a user may decrease. The receiver may be configured to automatically adjust receiver display settings or adjust how information is displayed in order to attract greater attention to the receiver from the user as glucose levels become increasingly high or low. For example, the receiver may automatically adjust the screen contrast so that it progressively increases as glucose levels rise or fall. The receiver may also increase the color saturation to attract greater attention. Font sizes or shapes may also be adjusted to be more pronounced, for example by increasing font size or by applying a bold-face to displayed text. Furthermore, the receiver screen may be configured to blink in order to attract further attention, for example, when glucose levels reach extremes. As one example, a person's normal glucose level may be 120 mg/dl while a high glucose threshold for the person may be 200 mg/dl. When the person's glucose level is at the normal level, the screen contrast may be set at 50% and all fonts sizes may be normal. As glucose levels for the person increases, the intensity of the backlight may progressively increase to become brighter, the contrast may be increased such that trend graphs go from grey to black, and color may be displayed more vibrantly. Additionally, font sizes may be increased. When the person's glucose level reaches the high level of 200 mg/dl, the screen backlight may start to blink on and off to further attract a user's attention. Similar adjustments may automatically be made as the user's glucose level reaches a low glucose threshold.

Alarm Volume

In another embodiment, alarm volumes may be automatically adjusted to attract greater attention to the receiver from the user as glucose levels become increasingly high or low. For example, as a glucose level becomes progressively lower, an alarm's volume might be automatically adjusted to become progressively louder. In addition, a louder alarm may be more effective at lower glucose levels than at higher glucose levels. As a result, in another embodiment, the alarm value may be increased as a glucose level falls, but not be increased as a glucose level rises. As one example, if a person's glucose levels are normal, an alarm (or alert) volume may be set at 50% of the potential volume. As the person's glucose level falls, the alarm volume might be progressively increased until the user reaches a low level threshold, at which point the alarm or alert would be played at 100% of the potential volume. As glucose levels fall below the low threshold, the volume may be continued to be played at 100% of the potential volume. Furthermore, as the person's glucose level rises, the alarm volume might also be progressively increased until the user reaches a high level threshold, at which point an alarm or alert may be played at 100% of the potential volume. FIG. 15A shows a table illustrating alarm volumes which correspond to various glucose levels. FIG. 15B shows a chart showing the percentage of system volume which correspond to various glucose levels. Furthermore, in one aspect, current alarms may be adjusted by the user for volume by alarm type, but the alarm volume options may be preset.

Emergency Response Instructions

Under certain circumstances, a person with extremely low glucose levels may lose consciousness. A device may be configured to determine that a user may have lost consciousness and that the user would need further assistance from others. For example, when a receiver detects that a glucose level is below a determined value (e.g., below 60 mg/dl), and that the user has not responded to an alarm (e.g., no button has been pressed for 10 minutes), the receiver may determine that a user may have lost consciousness. Other sensors or indicator could be used to confirm this indication, for example, an accelerometer (e.g., indicating no movement), a sweat indicator, a temperature sensor, a heart rate monitor, or the like. In this event, a device may switch to a mode that triggers an alarm type used to alert others of the user's medical condition. In one aspect, this mode may be described as an emergency response instruction mode. In this mode, an alarm may be changed to a voice that calls for help. For example, the alarm type may be a voice that says "Call 911. Help. Press a button for more information." The alarm may be repeated until another person (e.g., a bystander) pushes a button. After a button is pushed, the device may further instruct the bystander to aid the unconscious person by instructing the user to look for a glucogon shot in the patient's belongings. The device may also indicate to the bystander what information to communicate to an emergency response operator. This information may include the current glucose level and the time the glucose level fell below a determined threshold.

Computer Peripheral Device

The receiver may additionally be configured to be connected to another computing device and be recognized as a peripheral device. The receiver may be configured such that it implements a standard input/output interface such that the computer recognizes the receiver as a standard input/output device. For example, a receiver may be configured to be recognized as a webcam. By using a standard input/output interface, glucose data and other information may be shared with the computer and other networks using existing applications and without further modification or defining a custom input/output interface. Glucose information could be shared using existing or future applications such as with Skype (e.g., through a screen sharing feature), WebEx, GoToMeeting, iChat, or any other application configured to use a peripheral device such as a webcam. As one example, a user may have a consultation with a medical professional online. The user may start a video conversation, for example, with the medical professional and may wish to share glucose information during the course of the consultation. To share the glucose information, the user would connect the glucose receiver device to the computer via a connection cable. Because the computer would recognize the receiver as a webcam device, the user would be able to select the receiver device as the current video output device and the glucose data displayed on the receiver screen is shared with the medical professional.

Touchscreen Gestures

As described above, a receiver may include a touch screen for receiving touch input. Touch input from the user may be used to determine what type of information is displayed by the receiver. For example, if a user swipes a finger across the top and down the side of the touchscreen, the receiver might be configured to display the current glucose value and/or output the current glucose value audibly. In another example, a user may simply tap the screen to display the current glucose value. Different touchscreen gestures might be defined to display the current glucose value, a current trend in glucose data, a trend for the last thirty minutes, a trend for the last sixty minutes, or a trend for the last ninety minutes.

In another embodiment, the receiver might respond to a user touchscreen gesture without using a visual display, but instead use vibrations to communicate glucose information. For example, to communicate a specific glucose reading, a series of short vibrations may be used to communicate each digit, while a longer vibration may signify a change in the digits. As one example, to communicate 135 mg/dL, the following vibrations might take place:

1 short vibration followed by 1 long vibration
3 short vibrations followed by 1 long vibration
5 short vibrations followed by 1 long vibration In addition to communicating single numbers, a vibration length may also communicate glucose trends or rises and falls in glucose levels. For example, an increasing glucose may be communicated by outputting a series of vibrations with increased length. Conversely, falling glucose may be communicated by having a series of decreasing length vibrations. Using touchscreen gestures and/or vibrations may aid a user in understanding glucose information without looking at the receiver display or for communicating glucose information to the visually impaired.

SUMMARY

All of the processes described above may be embodied in, and fully automated via, software code modules executed by one or more general computing devices, including mobile computing devices. The code modules may be stored in any type of computer-readable medium or other computer storage device. Some of all of the methods may alternatively be embodied in specialized computer hardware. In addition, the components referred to herein may be implemented in hardware, software, firmware, or a combination thereof.

Any process descriptions, elements, or blocks in the flow diagrams described herein and/or depicted in the attached figures should be understood as potentially representing modules, segments, or portions of code that include one or more executable instruction for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

The software, data, and/or components described above may be stored on a computer readable medium and loaded into memory of a computer device including downloading, using a drive mechanism associated with a computer readable medium that stores the data, such as a flash drive, CD-ROM, DVD-ROM, network interface or the like. Further, the component and/or data can be included in a single device or distributed in any manner.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated.

It is understood that any specific order or hierarchy of steps in any disclosed process is an example of a sample approach. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A method for presenting an interactive glucose chart on a display device, comprising:
   displaying on a touch-sensitive display of a computing device a glucose trend chart displaying monitored glucose levels of a host over a first time range;
   displaying on the display a navigation bar simultaneously with the glucose trend chart, the navigation bar displaying a graph of the monitored glucose levels of the host over a second time range that is greater than and encompasses the first time range, wherein predetermined user interaction with the navigation bar detected by the computing device changes the first time range of glucose data; and
   displaying event data associated with the monitored glucose levels on the glucose trend chart at a particular point in time when a corresponding event occurred, the event data including one or more of a calibration reference event, insulin delivery event, a meal event, or an activity event,
   wherein the displaying the event data includes presenting an icon illustrative of the event type proximate to a glucose trend line of the glucose trend chart corresponding to the particular point in time.

2. The method of claim 1, wherein the navigation bar is positioned adjacent to the glucose trend chart on the display.

3. The method of claim 1, wherein the navigation bar includes an indication of the first time range.

4. The method of claim 3, wherein the graph of the navigation bar displays the glucose data encompassed by the first time range differently than the glucose data not encompassed by the first time range.

5. The method of claim 4, wherein the glucose data encompassed by the first time range displayed on the navigational bar is shaded differently than the data not encompassed by the first time range.

6. The method of claim 3, wherein the indication of the first time range includes a selectable slider bar that can be touched and dragged by a user across the navigational bar to change the first time range.

7. The method of claim 3, further comprising increasing a resolution of the glucose trend chart responsive to detecting a predefined user input using the touch-sensitive display.

8. The method of claim 7, wherein the predefined user interaction comprises detecting user movement along a y-axis direction of the glucose chart.

9. The method of claim 1, further comprising labeling one or more peaks or valleys of the glucose trend chart with a glucose level of each of the one or more peaks or valleys.

10. The method of claim 9, wherein labeling further comprises indicating a time associated with each of the one or more peaks or valleys.

11. The method of claim 1, further comprising:
displaying additional data associated with the event data at the particular point in time responsive to detecting a predefined user gesture over the particular point in time on the glucose trend chart.

12. The method of claim 11, wherein the predefined user gesture comprises tapping of, selecting of or expanding the glucose trend chart that corresponds to the particular point in time.

13. The method of claim 11, wherein the predefined user gesture includes a sequence of two or more gestures on the touch-sensitive display.

14. The method of claim 13, wherein the sequence of two or more gestures includes a first swiping gesture in a first direction followed by a second swiping gesture in a second direction different than the first direction.

15. The method of claim 1, further comprising:
displaying one or more of a current glucose value, a current trend value of the monitored glucose levels, or a glucose trend based on a period of time responsive to detecting a predefined sequence of two or more user gestures on the touch-sensitive display.

16. The method of claim 15, wherein the two or more user gestures includes a first swiping gesture in a first direction followed by a second swiping gesture in a second direction different than the first direction.

* * * * *

UNITED STATES PATENT AND TRADEMARK OFFICE
CERTIFICATE OF CORRECTION

PATENT NO.        : 9,498,164 B2
APPLICATION NO.   : 14/098366
DATED             : November 22, 2016
INVENTOR(S)       : Johnson et al.

Page 1 of 1

It is certified that error appears in the above-identified patent and that said Letters Patent is hereby corrected as shown below:

On the Title Page

Column 2 page 4, item (56) Line 8, Under Other Publications, change "Biosensros" to --Biosensors--.

Column 2 page 4, item (56) Line 10, Under Other Publications, change "Continous" to --Continuous--.

In the Specification

Column 16 Line 11, Change "hyperglycemica," to --hyperglycemia,--.

Column 23 Line 66, Change "glucogon" to --glucagon--.

Signed and Sealed this
Sixth Day of June, 2017

Michelle K. Lee
*Director of the United States Patent and Trademark Office*